United States Patent
Peng et al.

(10) Patent No.: US 12,215,115 B2
(45) Date of Patent: Feb. 4, 2025

(54) PLATINUM (II) TETRADENTATE ONNO COMPLEX LUMINESCENT MATERIAL, PREPARATION METHOD AND APPLICATION THEREOF IN ORGANIC LIGHT EMITTING DIODE

(71) Applicant: GUANGDONG AGLAIA OPTOELECTRONIC MATERIALS CO., LTD, Guangdong (CN)

(72) Inventors: Jiahuan Peng, Foshan (CN); Huiyang Li, Foshan (CN); Lei Dai, Foshan (CN); Lifei Cai, Foshan (CN)

(73) Assignee: GUANGDONG AGLAIA OPTOELECTRONIC MATERIALS CO., LTD, Foshan (CN)

( * ) Notice: Subject to any disclaimer, the term of this patent is extended or adjusted under 35 U.S.C. 154(b) by 752 days.

(21) Appl. No.: 17/297,741

(22) PCT Filed: Nov. 2, 2019

(86) PCT No.: PCT/CN2019/115177
§ 371 (c)(1),
(2) Date: May 27, 2021

(87) PCT Pub. No.: WO2020/125238
PCT Pub. Date: Jun. 25, 2020

(65) Prior Publication Data
US 2022/0081458 A1    Mar. 17, 2022

(30) Foreign Application Priority Data

Dec. 17, 2018 (CN) .......................... 201811544427.2

(51) Int. Cl.
| C07F 15/00 | (2006.01) |
| H10K 85/30 | (2023.01) |
| H10K 50/11 | (2023.01) |
| H10K 101/10 | (2023.01) |

(52) U.S. Cl.
CPC ....... C07F 15/0086 (2013.01); H10K 85/346 (2023.02); *H10K 50/11* (2023.02); *H10K 2101/10* (2023.02)

(58) Field of Classification Search
CPC .................................................. C07F 15/0086
See application file for complete search history.

(56) References Cited

U.S. PATENT DOCUMENTS

| 2003/0205707 A1 | 11/2003 | Chi-Ming |
| 2006/0264625 A1 | 11/2006 | Nakayama et al. |
| 2017/0162803 A1 | 6/2017 | Che et al. |

FOREIGN PATENT DOCUMENTS

| CN | 1649886 A | 8/2005 |
| CN | 1777663 A | 5/2006 |
| CN | 100509827 C | 7/2009 |
| CN | 105273712 A | 1/2016 |

OTHER PUBLICATIONS

Lin et al., "Structural, Photophysical, and Electrophosphorescent Properties of Platinum(II) Complexes Supported by Tetradentate N2O2 Chelates" Chem. Eur. J., Feb. 25, 2003, 9, 1263.
Zhou et al., "Efficient Red Electroluminescent Devices with Sterically Hindered Phosphorescent Platinum(II) Schiff Base Complexes and Iridium Complex Codopant", Chem. Asian. J., Aug. 21, 2014, 9, 2984.
Yong-Yue Lin et al. "Structural, Photophysical and Electrophosphorescent Properties of Platinum (II) Complexes Supported by Tetradentate N2O2 Chelates". Chem. Eur. J. 2003.
Liang Zhou et al. "Efficient Red Electroluminescent Devices with Sterically Hindered Phosphorescent Platinum (II) Schiff Base Complexes and Iridium Complex Codopant". Chemistry 2014.

*Primary Examiner* — John S Kenyon
(74) *Attorney, Agent, or Firm* — Maschoff Brennan

(57) ABSTRACT

The invention relates to a platinum (ii) tetradentate onno complex luminescent material, preparation method and application thereof in organic light emitting diode. A platinum (II) tetradentate pyridine diphenol ONNO complex light-emitting material having the chemical structure of Formula (I) can be used for manufacturing organic light-emitting diodes emitting pure red light. The light-emitting material of the invention, because the end of the left side thereof is connected to benzofuran, has more red shift than the emission spectrum of the bipyridyl phenol ONNO-Pt(II) complex without a benzofuran group, and the anti-aggregation performance of the platinum(II) complex is effectively increased, as a B group is introduced on the phenolic ring on the right side thereof, so the self-quenching rate constant is low, and the color purity emitting deep red light and better luminous efficiency can be maintained in a certain range of doping concentration, which is more suitable for industrial preparation systems.

20 Claims, No Drawings

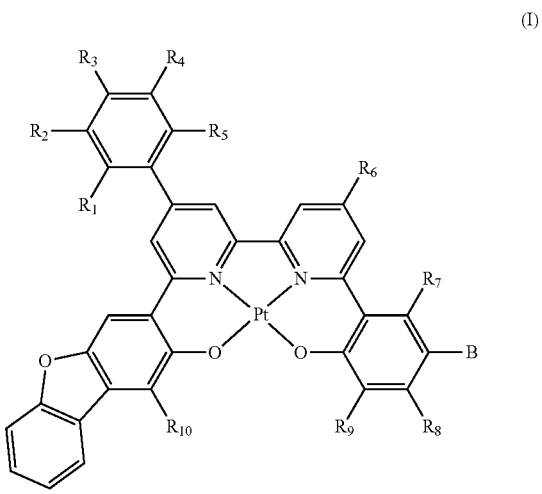

(I)

PLATINUM (II) TETRADENTATE ONNO COMPLEX LUMINESCENT MATERIAL, PREPARATION METHOD AND APPLICATION THEREOF IN ORGANIC LIGHT EMITTING DIODE

FIELD OF THE INVENTION

The invention relates to a class of organic metal materials with optimized structures, and the applications thereof in organic light-emitting diodes (OLED) and polymer light-emitting diodes (PLED), for which high-efficiency monochromatic OLEDs can be manufactured through a variety of technologies, including vacuum deposition, spin coating, or printing, with using the organic metal materials showing better emission quantum efficiency and better color purity.

BACKGROUND

OLED is namely an organic light-emitting diode or an organic light-emitting device. OLED is an independent light-emitting device without backlight, has characteristics such as fast response speed, low driving voltage, high light-emitting efficiency, high resolution, and wide viewing angle, so it has already become a new generation of display and lighting technologies, especially with huge application prospects in mobile phones, computers, TVs, bendable and foldable electronic products.

There are currently two types of light-emitting material used in OLEDs: fluorescent materials and phosphorescent materials. The light-emitting materials used in early devices are mainly organic small-molecule fluorescent materials, and spin statistics quantum theory shows that the theoretical internal quantum efficiency of fluorescent materials is only 25%. In 1998, Professor Forrest of the Princeton University and Professor Thompson of the University of Southern California discovered the phosphorescent electroluminescence of metal organic complex molecular materials at room temperature. The strong spin-orbit coupling of heavy metal atoms can effectively promote the inter-system crossing (ISC) of electrons from singlet to triplet, so that OLED devices can make full use of the singlet and triplet excitons generated by electrical excitation to make the theoretical internal quantum efficiency of light-emitting material each 100% (Nature, 1998, 395, 151).

At present, many red light OLED materials have been synthesized, but high-efficiency deep red light materials are still lacking. The main reason is that the energy level difference between the lowest excited state and the ground state of the red light material is so small that the non-radiative inactivation of the excited state is prone to occur, in addition, the concentration quenching effect is obviously heightened in the high concentration or solid film. In order to reduce this concentration quenching, the red light materials are mostly doped into a subject material as a light-emitting layer.

In the red light Ir(III) complex, due to some structural constraints and strong intermolecular interactions, it often leads to unbalanced carrier injection/transport, luminescence quenching, and poor device efficiency. In order to solve such problems, researchers mainly introduce electron donor groups to enhance carrier injection/transport capabilities. These donor groups mainly include carbazole groups and quinoline groups. After introducing donor groups, the morphology and thermal stability of the complexes are enhanced, and the external quantum efficiency of devices is also significantly improved.

As the cyclometalated platinum complex has very good luminescence properties, the tetradentate cyclo-platinum (II) complex has gotten a widespread concern and good result, but the roll-off of efficiency is one of the most serious problems of platinum(II) complexes. Generally, the platinum(II) complex have a planar geometric structure and easily form an excimer. Therefore, only within a narrow range of doping concentration can the device with high color purity (about 1%-5% by weight) be effectively obtained. When the doping concentration is high, it is easy to form excimer emission, thereby influencing color purity and device stability, and the difficulty to optimize the performance of material and device will be increased by the narrow doping concentration range, which limits the industrial application of this type of material.

In 2003, Che reported a bipyridine diphenol ONNO-Pt(II) complex. Because of its high planarity and strong $\pi$-$\pi$ interaction accumulated between molecules, it is prone to form excimer at a slightly higher concentration. (Chem. Eur. J., 2003, 9, 1263; US20030205707/CN100509827). In 2010, Che added tert-butyl (Chem. Asian. J., 2014, 9, 2984) to the red Schiff base ONNO platinum(II) complex, but the $\pi$-$\pi$ interaction tightly accumulated between molecules can still be observed in the X-ray diffraction crystal structure. In 2014, Che introduced a bicyclic group with large steric hindrance into the red Schiff base ONNO platinum(II) complex by adopting the same method(Chem. Eur. J., 2010, 16, 233; CN105273712B), which can effectively reduce its self-quenching constant, but the maximum doping concentration in the study is only 7%. Therefore, how to obtain high efficiency and maintain ideal deep red light Pt-based materials in a wide range of doping concentration is an urgent problem to be solved in the industry and academia.

SUMMARY

For the defects in the above-mentioned fields, the invention describes a platinum (II) complex system with optimized structure, which has a simple synthesis process, a stable chemical structure, high anti-aggregation performance, and high emission quantum efficiency, and of which a high-efficient OLED with emitting pure red light can be made.

As platinum(II) complexes usually have a square planar geometric structure, at high doping concentrations, the platinum(II) complexes are prone to form self-aggregation, thereby forming excimer emission and influencing emission spectrum, color purity and device efficiency. In order to overcome this shortcoming, the invention provides a platinum (II) tetradentate ONCN complex light-emitting material having the chemical structure of Formula (I). The material still has strong anti-aggregation ability and high emission quantum efficiency at high doping concentration, which is more suitable for industrial preparation systems.

The invention further provides a preparation method of the light-emitting material and application thereof in organic light-emitting diodes (OLED).

A platinum (II) tetradentate pyridine diphenol ONCN complex light-emitting material has the chemical structure of Formula (I),

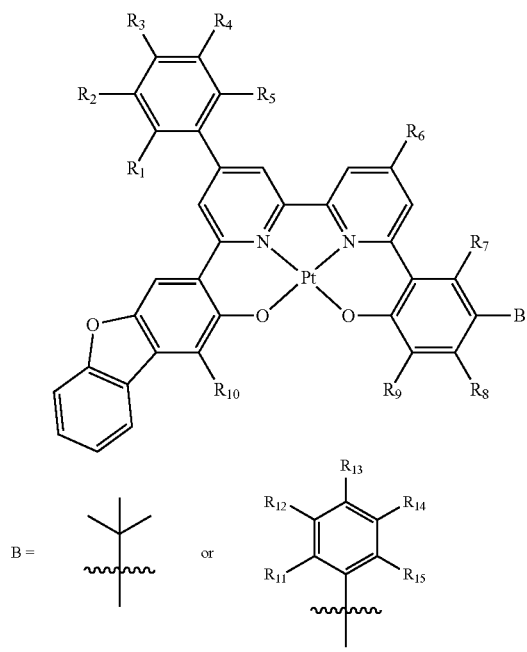

(I)

where $R_1$-$R_{10}$ are independently a hydrogen atom, a deuterium atom, a halogen, a hydroxyl group, an unsubstituted alkyl group, a halogenated alkyl group, a deuterated alkyl group, a cycloalkyl group, an unsubstituted aryl group, a halogenated aryl group, an acyl group, an alkoxyl group, an acyloxyl group, an amino group, a nitro group, an acylamino group, an aralkyl group, a cyano group, a carboxyl group, a sulfonyl group, a styryl group, an amino carboxyl group, a carbamoyl group, an aryloxy carboxyl group, a phenoxy carboxyl or epoxy carboxyl group, a carbazole group or a diphenylamine group, or $R_1$-$R_{10}$ independently form a 5-8 membered ring with adjacent groups, and $R_1$-$R_{10}$ are not hydrogen at the same time; B presents an anti-aggregation group, wherein $R_{11}$-$R_{15}$ are independently a hydrogen atom, a deuterium atom, a halogen, an unsubstituted alkyl group, a halogenated alkyl group, a deuterated alkyl group, a cycloalkyl group, an unsubstituted aryl group, a halogenated aryl group, a C1-C10 alkyl substituted aryl group, a cyano group, a carbazolyl group, or a C1-C10 alkyl substituted carbazolyl group.

The halogen or halogenation used in the invention includes fluorine, chlorine or bromine, more preferably F or Cl, most preferably F.

Where $R_1$-$R_{10}$ are independently a hydrogen atom, a deuterium atom, a halogen, a hydroxyl group, an unsubstituted alkyl group having 1 to 6 carbon atoms, a halogenated alkyl group having 1 to 6 carbon atoms, a deuterated alkyl group having 1 to 2 carbon atoms, a five- or six-membered cycloalkyl group, an unsubstituted aryl group having 6 to 10 carbon atoms, a halogenated aryl group having 6 to 10 carbon atoms, an alkoxyl group having 1 to 6 carbon atoms, an amino group, a nitro group, a cyano group, a carbazolyl group, or a diphenylamine group, or $R_1$-$R_{10}$ independently form a 5-8 membered ring with adjacent groups, and $R_{11}$-$R_{15}$ are independently a hydrogen atom, a deuterium atom, a halogen, an unsubstituted alkyl group having 1 to 6 carbon atoms, a halogenated alkyl group having 1 to 6 carbon atoms, a five- or six-membered cycloalkyl group, an unsubstituted aryl group having 6 to 10 carbon atoms, a halogenated aryl group having 6 to 10 carbon atoms, a C1-C4 alkyl substituted aryl group having 6 to 10 carbon atoms, a cyano group, a carbazolyl group, or a C1-C4 alkyl substituted carbazolyl group.

Preferably, $R_7$, $R_8$ are independently a hydrogen atom.

Preferably, $R_6$, $R_9$ and $R_{10}$ are independently a hydrogen atom, a fluorine atom, an unsubstituted alkyl group having 1 to 4 carbon atoms, a trifluoromethyl group or a phenyl group.

Preferably, $R_1$-$R_5$ are independently a hydrogen atom, a deuterium atom, a fluorine atom, an unsubstituted alkyl group having 1 to 4 carbon atoms, a halogenated alkyl group having 1 to 4 carbon atoms, a five- or six-membered cycloalkyl group, an unsubstituted aryl group having 6 to 10 carbon atoms, a fluorinated aryl group having 6 to 10 carbon atoms, and $R_{11}$-$R_{15}$ are independently a hydrogen atom, a deuterium atom, a fluorine atom, an unsubstituted alkyl group having 1 to 4 carbon atoms, a fluorinated alkyl group having 1 to 4 carbon atoms, a five- or six-membered cycloalkyl group, an unsubstituted aryl group having 6 to 10 carbon atoms, a halogenated aryl group having 6 to 10 carbon atoms, a C1-C4 alkyl substituted aryl group having 6 to 10 carbon atoms, a carbazolyl group, or a C1-C4 alkyl substituted carbazolyl group.

Where $R_1$-$R_5$ are independently a hydrogen atom, a fluorine atom, an unsubstituted alkyl group having 1 to 4 carbon atoms, a trifluoromethyl group or a phenyl group.

More preferably, $R_1$, $R_3$, $R_5$ are independently a hydrogen atom. Preferably, $R_2$, $R_4$ are independently a hydrogen atom, a fluorine atom, an unsubstituted alkyl group having 1 to 4 carbon atoms, a trifluoromethyl group or a phenyl group.

$R_{11}$-$R_{15}$ are independently a hydrogen atom, an unsubstituted alkyl group having 1 to 4 carbon atoms, a trifluoromethyl group or a phenyl group.

More preferably, $R_{12}$, $R_{14}$ are independently a hydrogen atom, $R_{11}$, $R_{13}$, $R_{15}$ are independently a hydrogen atom, a fluorine atom, an unsubstituted alkyl group having 1 to 4 carbon atoms, a trifluoromethyl group, a phenyl group, a 4-tert-butylphenyl group, a naphthyl group or a carbazolyl group.

Some specific non-limiting examples of the platinum (II) complexes having the Formula (I) are as below:

Complex 1001

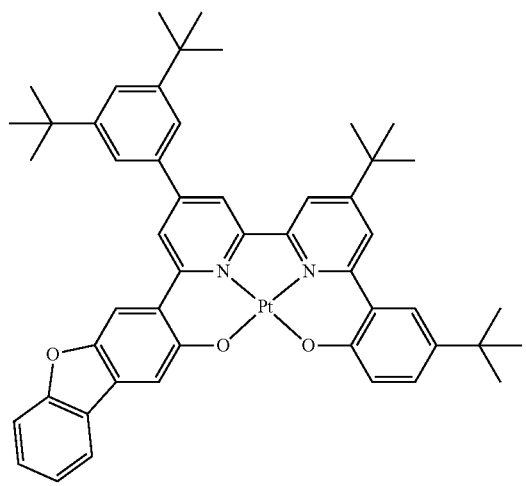

Complex 1002
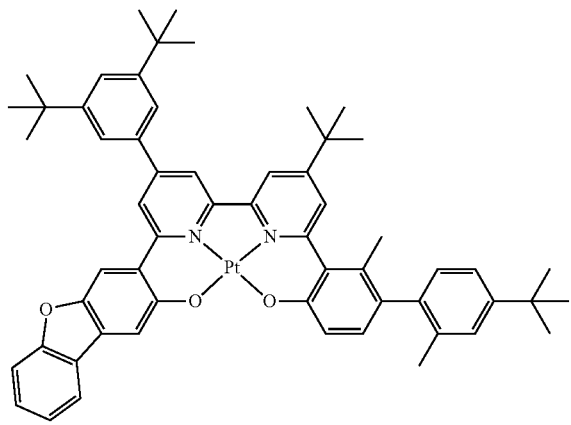
Complex 1003
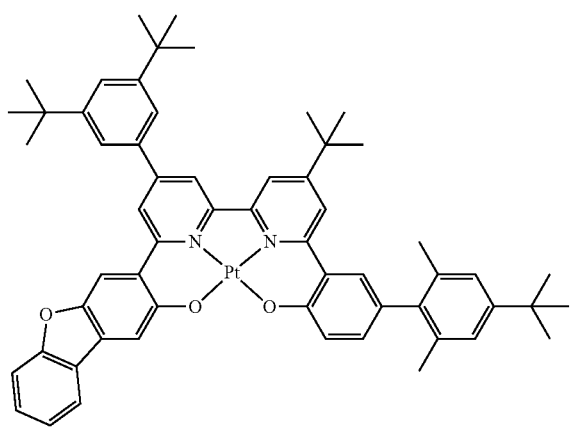
Complex 1004
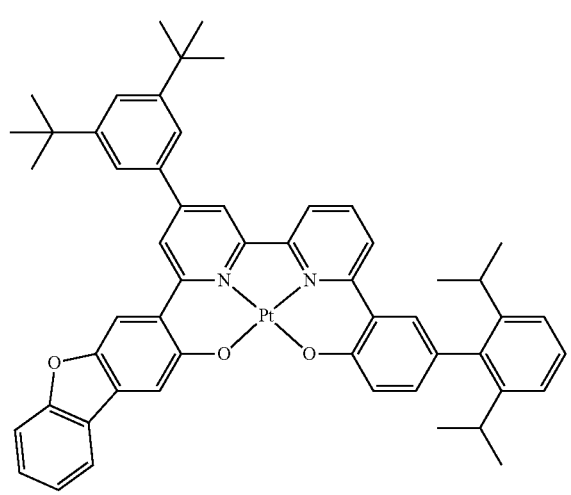
Complex 1005
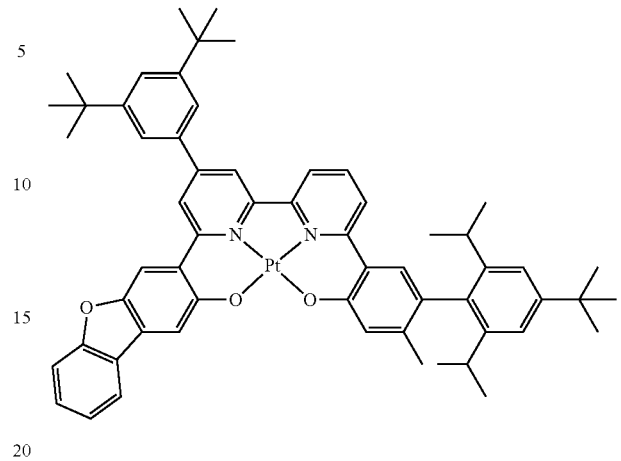
Complex 1006
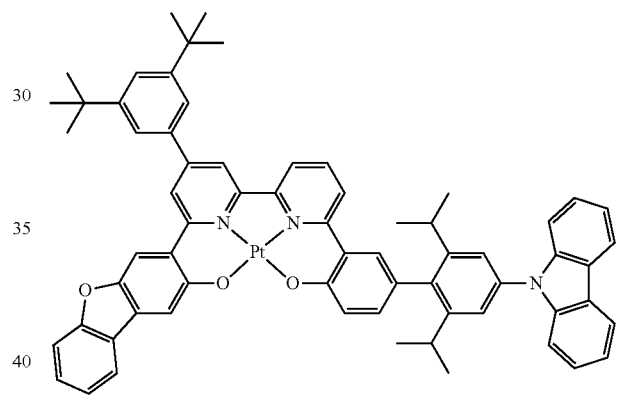
Complex 1007
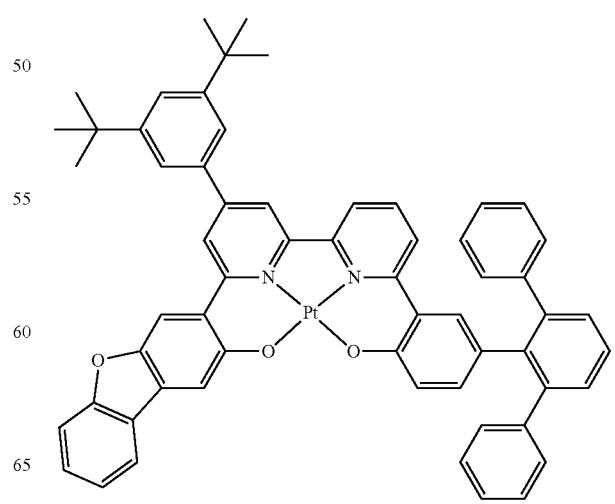

Complex 1008
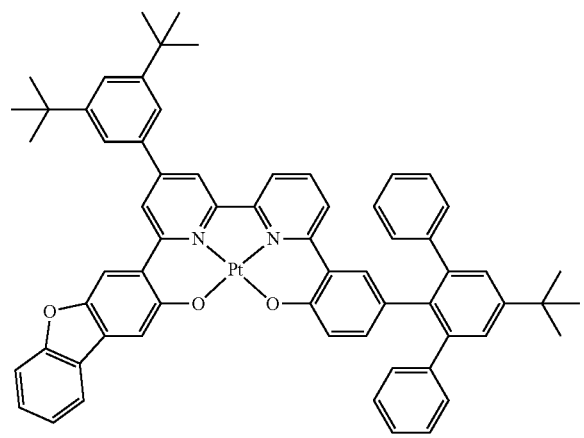
Complex 1011
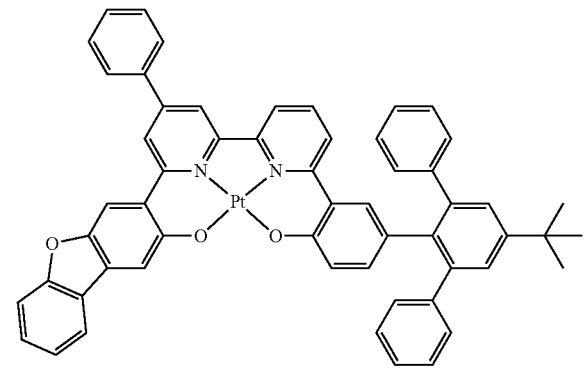
Complex 1009
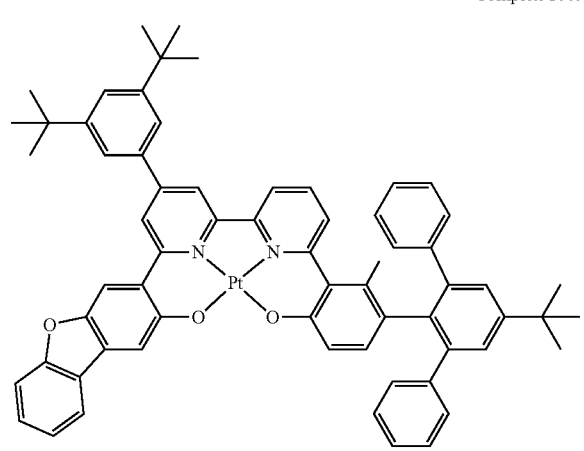
Complex 1012
Complex 1010
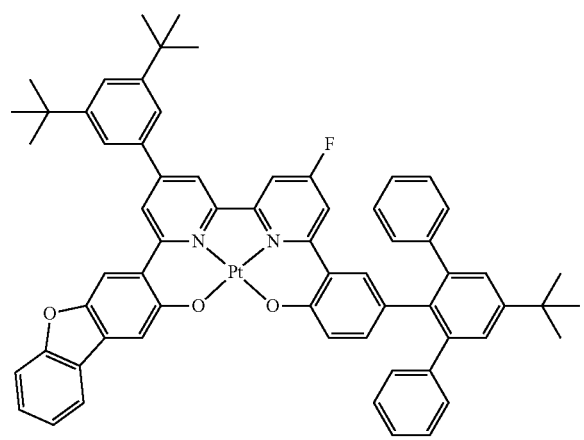
Complex 1013

Complex 1014
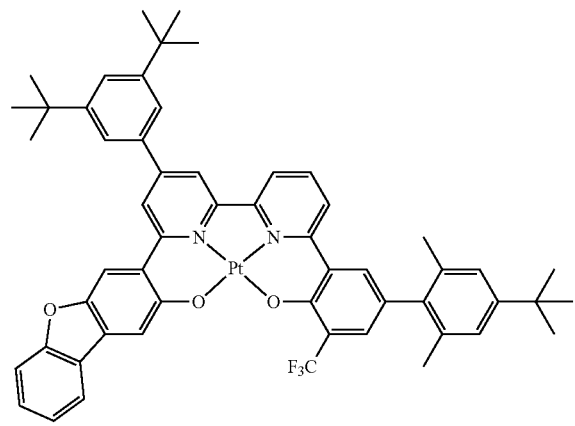
Complex 1015
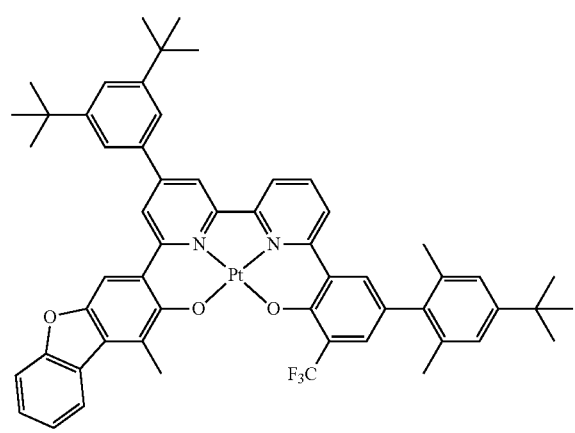
Complex 1016
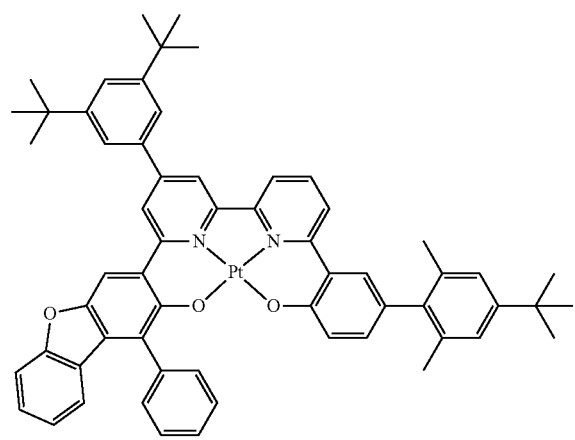
Complex 1017
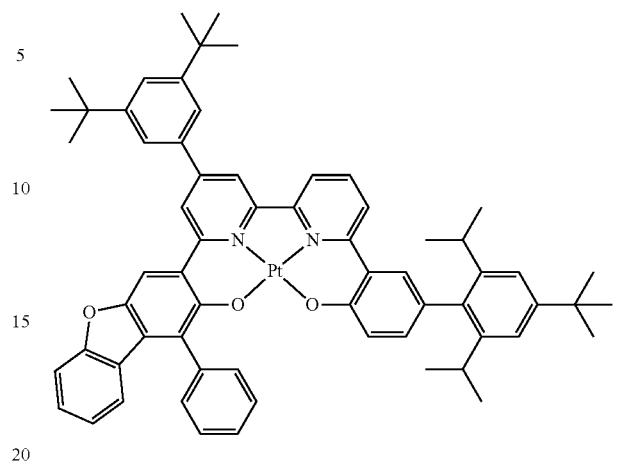
Complex 1018
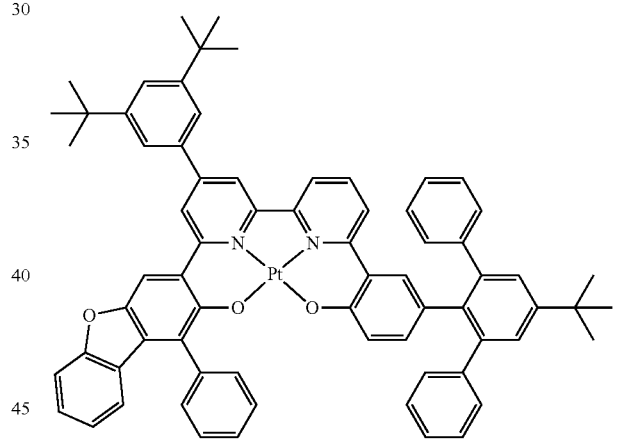
Complex 1019
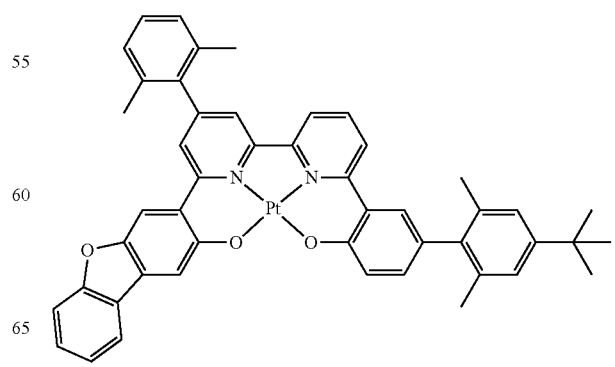

Complex 1020
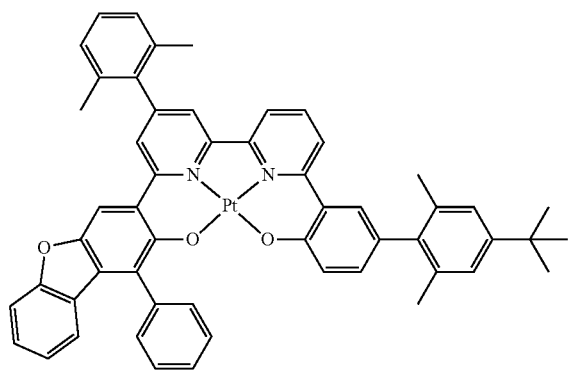
Complex 1021
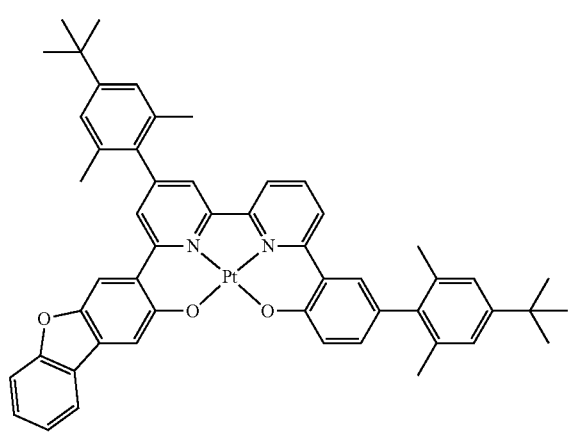
Complex 1022
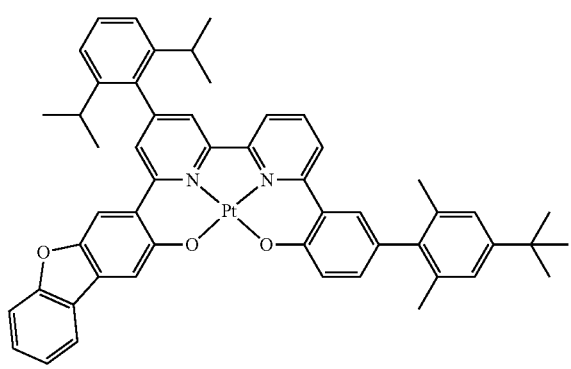
Complex 1023
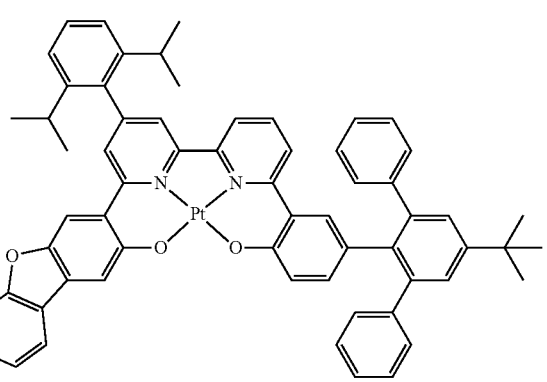
Complex 1024
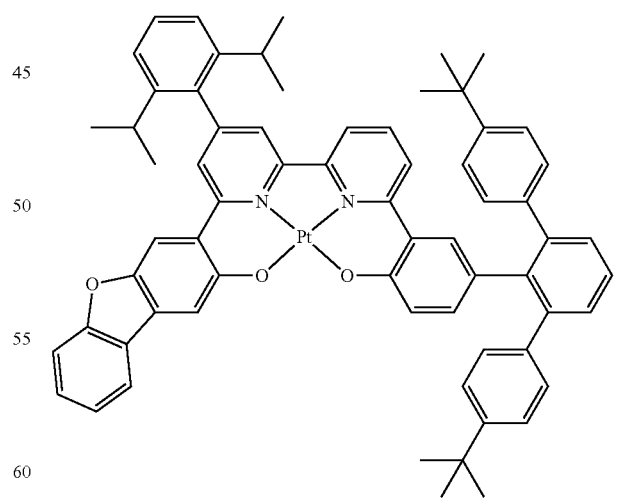
The metal-complex phosphorescent materials of the invention can be manufactured according to the method of the following chemical equation, but are not limited to the following method:

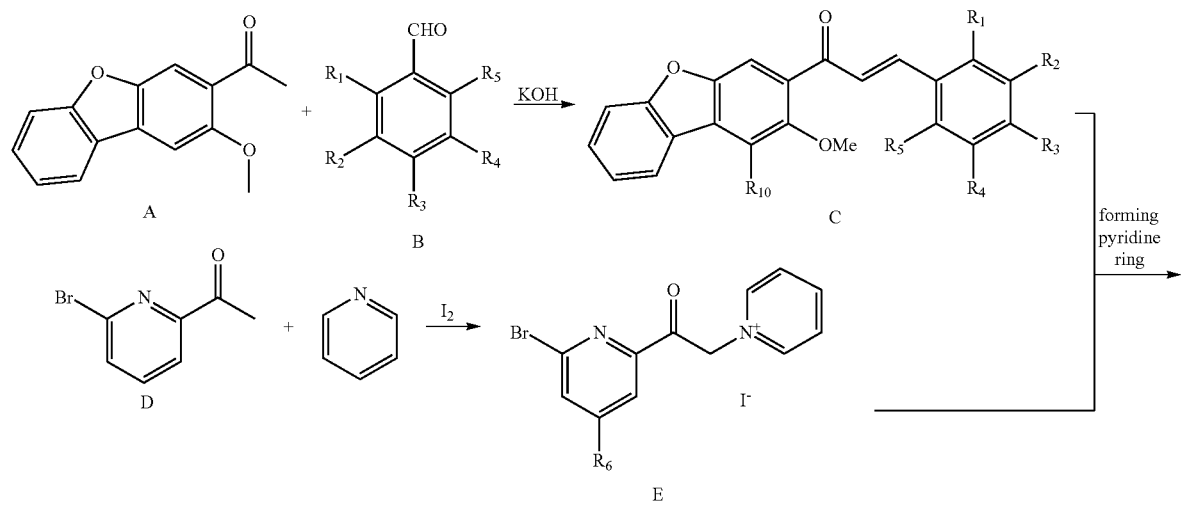
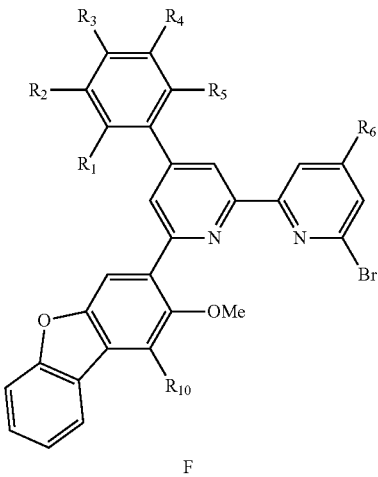
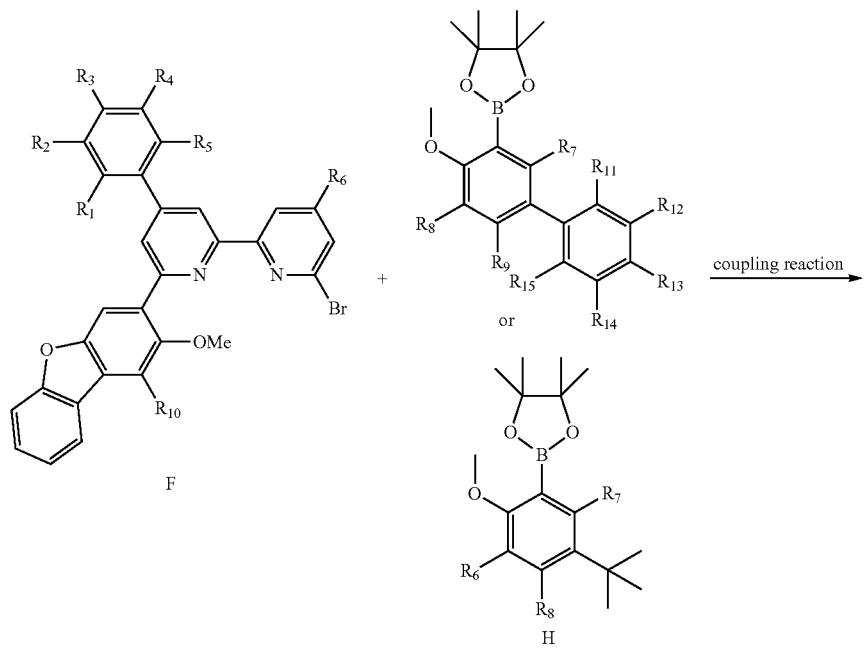

-continued
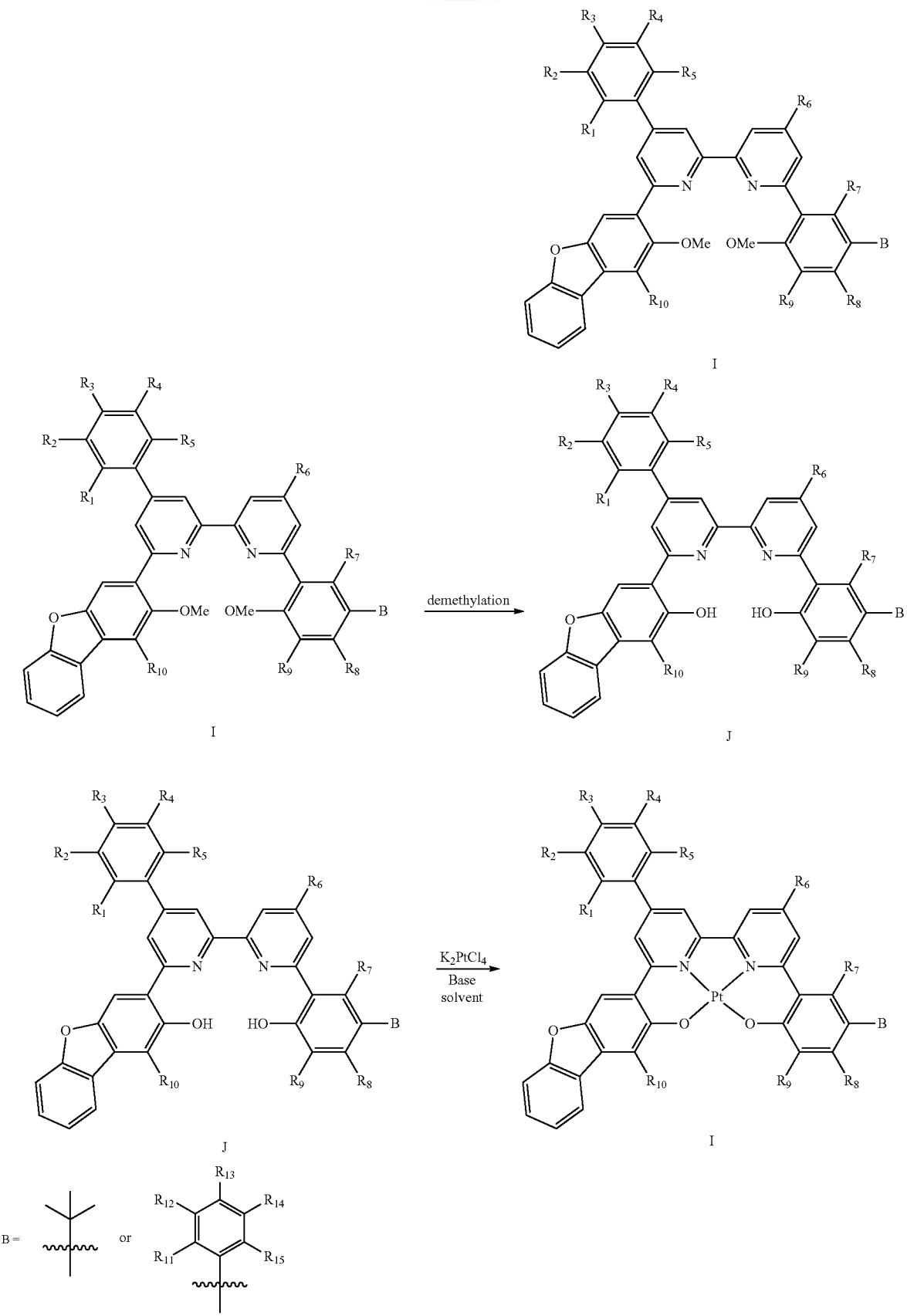

A $R_{10}$ substituted o-methoxydibenzo[b,d] furan ethyl ketone compound A and a substituted or unsubstituted benzaldehyde compound B are used as raw material to obtain a substituted or unsubstituted chalcone compound C under alkaline KOH conditions. A substituted or unsubstituted 6-bromopyridyl ethyl ketone compound D is mixed with such pyridine as a solvent to obtain a pyridine salt intermediate E under iodine simple substance conditions. A pyridine ring intermediate F is obtained from the substituted or unsubstituted chalcone compound C and the pyridine salt intermediate E under ammonium acetate conditions. The pyridine ring intermediate F is coupled with a o-methoxyphenyl boronic ester compound H by way of metal coupling (for example, carried out by using $Pd(PPh_3)_4$ as a catalyst and under $K_2CO_3$ alkali conditions) to obtain an intermediate I. A ligand J is obtained from the intermediate I by way of demethylation reaction. The ligand J reacts with a platinum compound (such as potassium tetrachloroplatinate) in a suitable solvent, at a suitable temperature and under alkaline conditions, to obtain a platinum (II) tetradentate ONNO complex light-emitting material after being purified.

A general method for synthesizing such a compound of the platinum (II) tetradentate pyridine diphenol ONCN complex light-emitting material is provided as above. The reaction materials, the reaction conditions and the amount of usage thereof can be appropriately adjusted according to the specific reaction conditions, not limited to the above range; the reaction time and temperature according to the reaction conditions can also be adjusted, not limited to the above range.

One or two or more of the platinum (II) tetradentate pyridine diphenol ONNO complex light-emitting materials according to the invention are applied in a light-emitting layer of an organic light-emitting device. The complex having the Formula (I) can be adopted to form a thin film by vacuum deposition, spin coating, inkjet printing or other known preparation methods. The compounds of the invention have been used as light-emitting materials or as dopants in a light-emitting layer to manufacture different multilayer OLEDs. Specifically, the platinum (II) tetradentate pyridine diphenol ONNO complex light-emitting material according to the invention can be used as a light-emitting layer of ITO/HAT-CN/TAPC/complex: CBP (x wt %)/Balq/Alq$_3$/LiF/Al, but not limited to the above device structure.

The platinum (II) tetradentate pyridine diphenol ONNO complex having the Formula (I) has medium solution quantum yield.

Because the platinum (II) tetradentate pyridine diphenol ONNO complex of the Formula (I) has a strong rigid structure, it can effectively decrease the energy consumed by molecular vibration and lessen non-radioactive decay, so high emission quantum efficiency can be obtained. High-efficiency organic diodes (OLEDs) emitting deep red light can be manufactured by using these complexes as light-emitting materials.

The organic metal complex having the chemical structure of the Formula (I), because the end of the left side thereof is connected to benzofuran, has more red shift than the emission spectrum of the bipyridyl phenol ONNO-Pt(II) complex without a benzofuran group, and the anti-aggregation performance of the platinum(II) complex is effectively increased, as

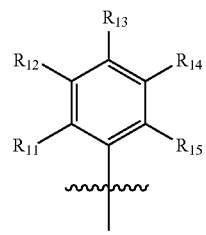

or a tert-butyl group is introduced on the phenolic ring on the right side thereof, so the self-quenching rate constant is low, and the color purity emitting deep red light and better luminous efficiency can be maintained in a certain range of doping concentration.

BRIEF DESCRIPTION OF THE DRAWINGS

Detailed Description of the Preferred Embodiments

Examples are provided for describing the implementation of the invention as below. These examples should not be deemed as a limitation. Unless otherwise mentioned, the percentage is all calculated by weight, and the proportion of solvent mixtures is all calculated by volume.

Example 1—Synthetizing Intermediate 3101

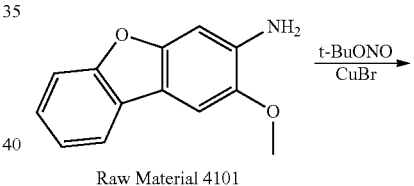

Raw Material 4101

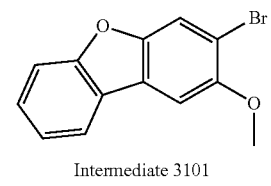

Intermediate 3101

A round-bottom flask is filled with the Raw Material 4101 (0.1 mol), tert-butyl nitrite (0.1 mol), cuprous bromide (0.12 mol) and acetonitrile (200 ml), and the reaction mixture is heated to 90° C. under a nitrogen atmosphere and stirred for 4 hours. After cooled to room temperature, the reaction mixture is added to with water, then extracted by dichloromethane, after evaporating out an solvent, the solid product obtained is beaten with methanol at −20° C. A beige solid with yield of 60% is obtained by suction filtration and desiccation.

Example 2—Synthetizing Intermediate 3201

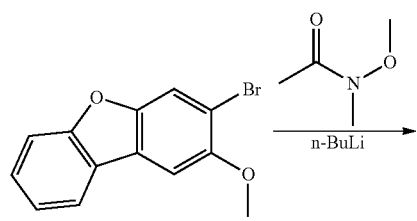

Intermediate 3101

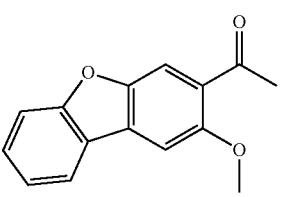

Intermediate 3201

The Intermediate 3201 (60 mmol) and dry tetrahydrofuran (100 mL) are put into a three-necked flask, stirred for 0.5 hours at −78° C. under a nitrogen atmosphere. Then, 1.2 molar equivalents of n-butyl lithium solution (2M) is slowly added dropwise, after stirring continues for 0.5 hour while maintaining the temperature, N-methoxy-N-methylacetamide (60 mmol) is added dropwise. Further, stirring continues for 1 hour while maintaining the temperature, then stirring is carried out overnight while the temperature slowly rises to room temperature. The reaction liquid is quenched by adding saturated ammonium chloride solution, and extracted by ethyl acetate, then organic phase solution is collected, and a crude product is separated by silica gel column chromatography, and then a solid is recrystallized with n-hexane, finally a pale pink solid with yield of 55% is obtained by suction filtration and desiccation.

Example 3—Synthetizing Intermediate 3301

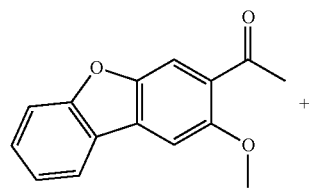

Intermediate 3201

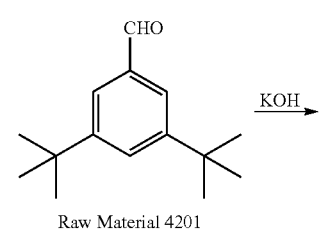

Raw Material 4201

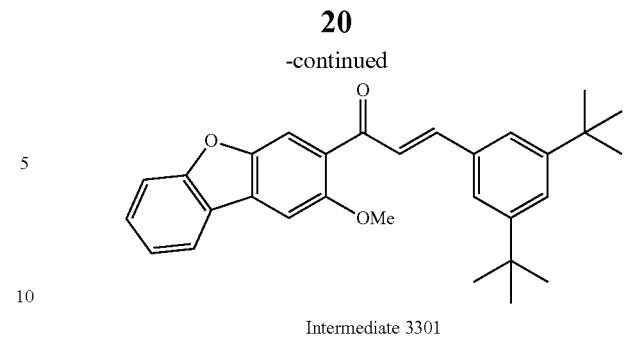

Intermediate 3301

A round-bottom flask is filled with the Intermediate 3201 (30 mmol), the Raw Material 4201 (33 mmol), which are stirred to dissolve by adding methanol (100 mL), then potassium hydroxide aqueous solution (10 mL, 50 mmol) is slowly added into the mixture dropwise. After finished adding, the reaction mixture is heated to 50° C. under a nitrogen atmosphere and stirred for 10 hours. After the reaction mixture is cooled to room temperature, 4 M HCl solution is added to adjust the pH of the mixture to neutralization. The solids filtered out by suction are dissolved in an organic solvent, after filtering out an insoluble substance, and removing a solvent, a solid product obtained is beaten with methanol at −20° C., finally a yellow solid with yield of 80% is obtained by suction filtration and desiccation.

Example 4—Synthetizing Intermediate 3401

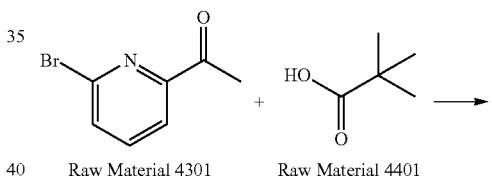

Raw Material 4301    Raw Material 4401

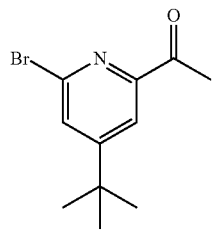

Intermediate 3401

The Raw Material 4301 (0.10 mol), the Raw Material 4401 (0.11 mol), ammonium persulfate (0.11 mol), silver nitrate (0.1 mol) and sulfuric acid solution are put into a three-necked flask and stirred at 110° C. for 15 hours. After finished reaction, the reaction fluid is cooled to room temperature with continuing stirring for 1 hour, then added to by water, and extracted by dichloromethane. After organic solution is collected, an solvent is removed, further the solid is beaten with methanol, a white solid with yield of 60% is obtained by suction filtration and desiccation.

Example 5—Synthetizing Intermediate 3501

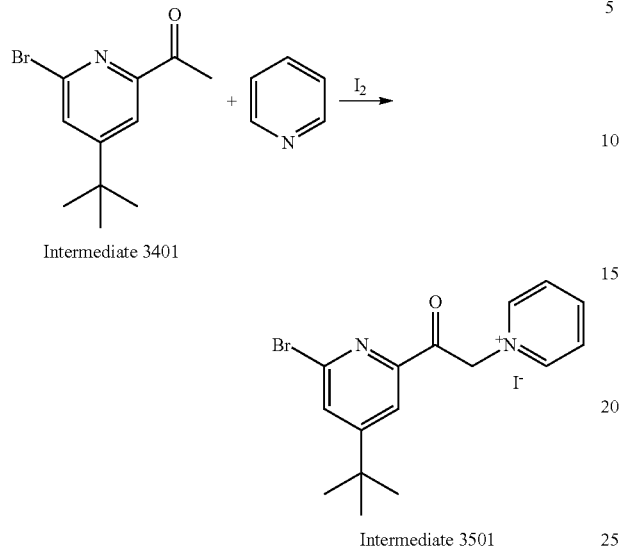

Intermediate 3401

Intermediate 3501

The Raw Material 3401 (0.05 mol), iodine (0.06 mol) and pyridine (100 mL) are put into a three-necked flask and stirred at 130° C. for 5 hours under a nitrogen atmosphere. After finished reaction, the reaction fluid is cooled to room temperature, an solvent, pyridine, is removed under reduced pressure, and a crude product is beaten with hot ethyl acetate, finally a light brown solid with yield of 50% is obtained by suction filtration and desiccation.

Example 6—Synthetizing Intermediate 3601

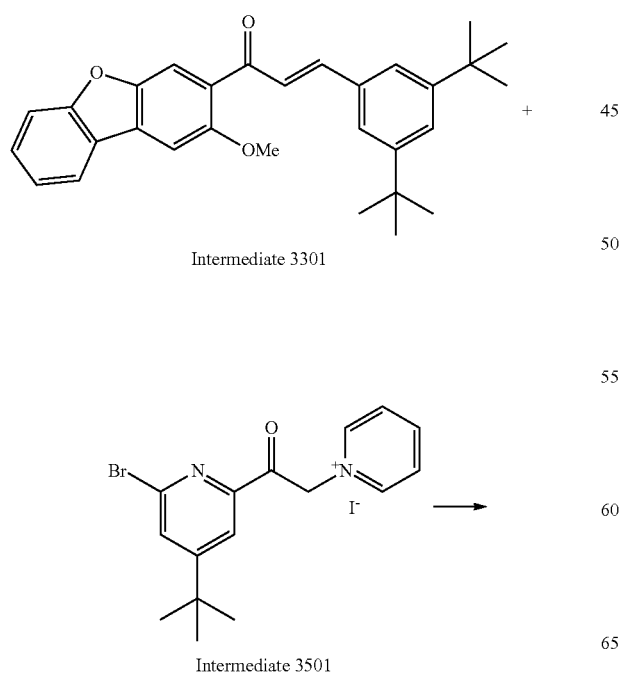

Intermediate 3301

Intermediate 3501

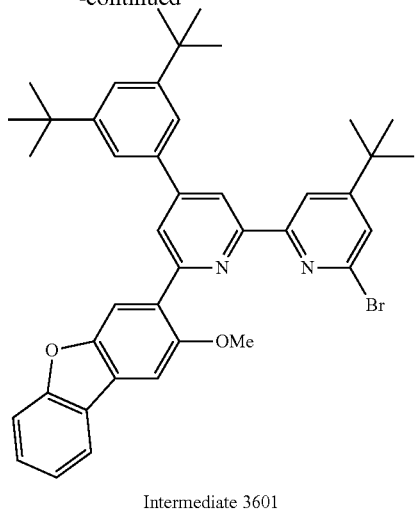

Intermediate 3601

The Intermediate 3301 (25 mmol), the Intermediate 3501 (25 mmol), ammonium acetate (250 mmol) and glacial acetic acid (100 mL) are put into a round-bottom flask, and stirred and refluxed at 130° C. for 2 hours under a nitrogen atmosphere. Under stirring, KOH is added to adjust the pH to neutralization, and then methanol is added to separate out a solid. The solid is beaten with methanol, finally a white solid with yield of 81% and purity of 98% is obtained by suction filtration and desiccation.

Example 7—Synthetizing Intermediate 3701

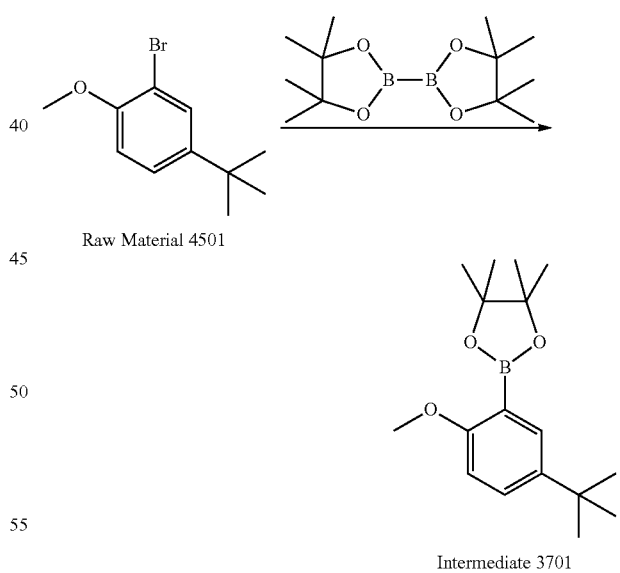

Raw Material 4501

Intermediate 3701

The Raw Material 4501 (50 mmol), pinacol diborate (52 mmol), Pd(dppf)Cl$_2$ (2.5 mmol), potassium acetate (0.1 mol) and dioxane (150 ml) are put into a round-bottom flask, and heated to reflux for 10 hours under a nitrogen atmosphere. After that, the dioxane is spun off, then water is added. The reaction liquid is extracted by ethyl acetate, after collecting an organic phase, a resolvent is spun off. An oily product with yield of 75% is obtained after being purified by silica gel column chromatography.

Example 8—Synthetizing Intermediate 3801

Example 9—Synthetizing Ligand 2001

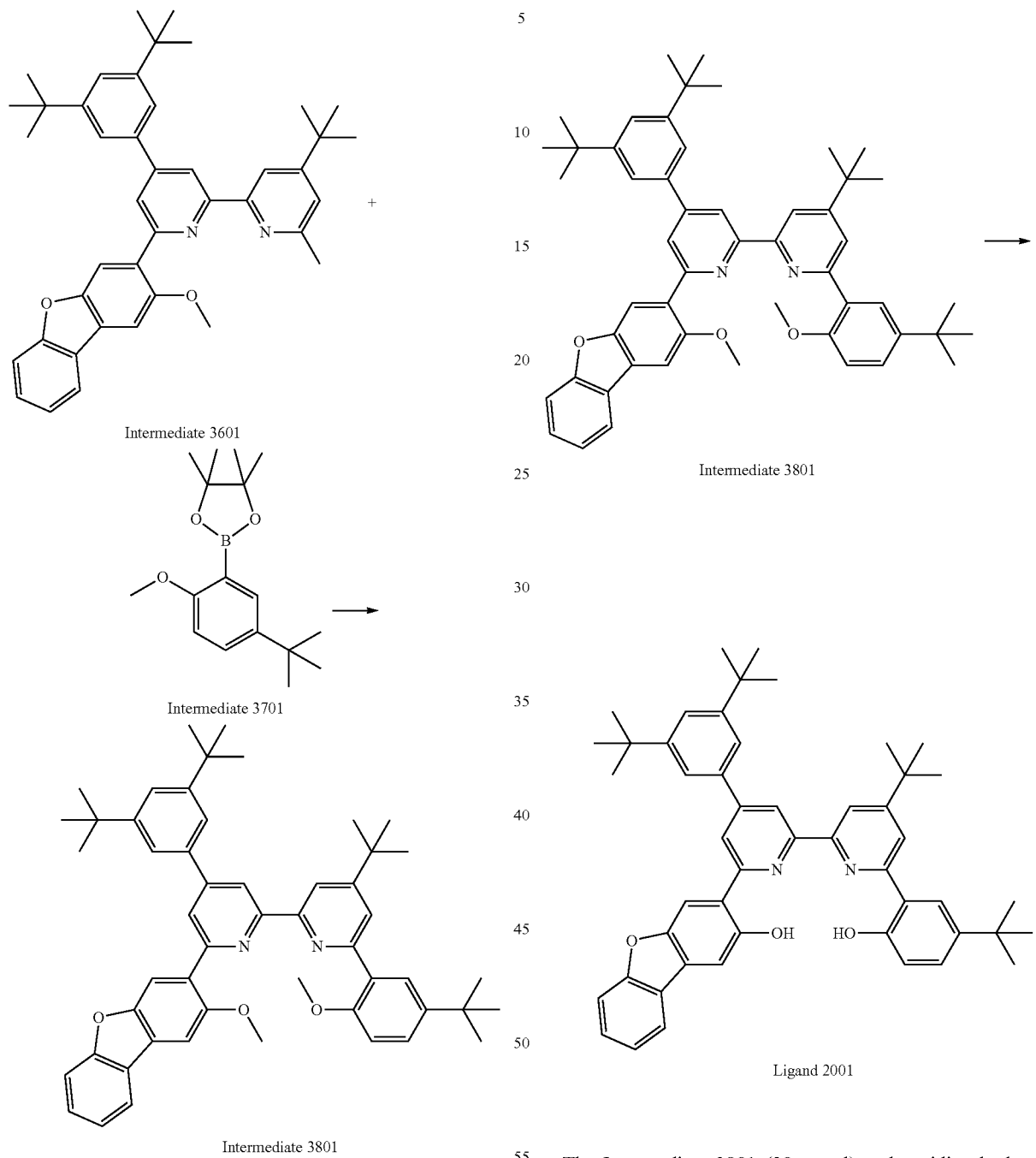

The Intermediate 3601 (30 mmol), the Intermediate 3701 (35 mmol), tetratriphenylphosphine palladium (3 mmol), potassium carbonate (60 mmol), dioxane (80 ml) ad water (20 ml) are put into a round-bottom flask, heated to reflux under a nitrogen atmosphere, react for 10 hours. After finished reaction, the dioxane is spun off, then the reaction liquid is extracted by dichloromethane, and organic phase solution is collected. A crude product is separated by silica gel column chromatography to obtain a foamy yellow solid with yield of 70%.

The Intermediate 3801 (20 mmol) and pyridine hydrochloride (40 g) are put into a round-bottom flask, heated to 200° C. under a nitrogen atmosphere until melt-out and stirred for 6 hours, after finished reaction and cooling, a large amount of water is added, thus the pyridine hydrochloride dissolves and a product is separated out, then the product is filtered out by suction and washed by water and methanol. Finally, an orange-yellow solid with yield of 85% is obtained by silica gel column chromatography.

Example 10—Synthetizing Complex 1001

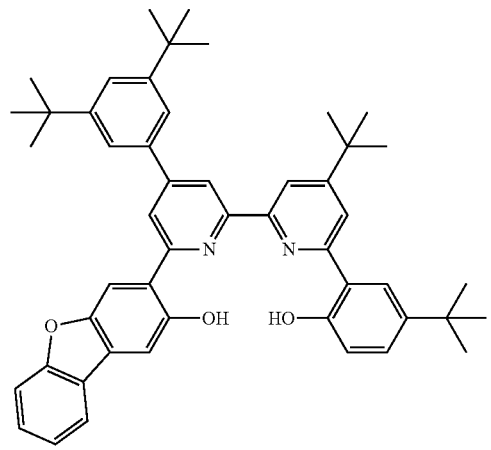

Ligand 2001

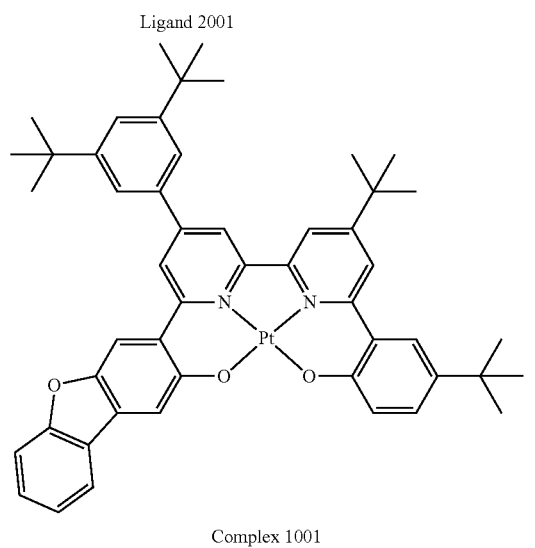

Complex 1001

The Ligand 2001 (15 mmol) is dissolved in dry DMSO where sodium tert-butoxide (35 mmol) and K₂PtCl₄ (35 mmol) are added, then the mixture is heated to 130° C. under a nitrogen atmosphere, and reacts for 12 hours. After finished reaction, it is cooled to room temperature naturally, and then an appropriate amount of water is added. A red solid is separated out. The solid is filtered out by suction and washed by water and methanol. The product is separated by silica gel column chromatography to obtain a red solid with yield of 76%. Ms(ESI): 924.4 (M+H).

Example 11—Synthetizing Intermediate 3108

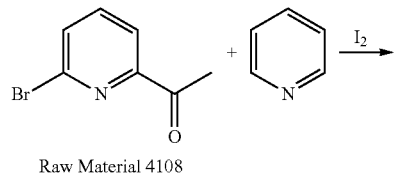

Raw Material 4108

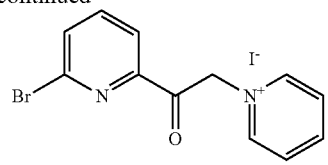

Intermediate 3108

The Raw Material 4108 (0.2 mol), iodine simple substance (0.205 mol) and pyridine (400 ml) are put into a round-bottom flask, heated to 130° C. under a nitrogen atmosphere, and reacted for 4 hours. After that, the pyridine is evaporated out under reduced pressure, the residue is heatedly beaten twice with ethyl acetate to obtain a light brown solid with yield of 60%.

Example 12—Synthetizing Intermediate 3208

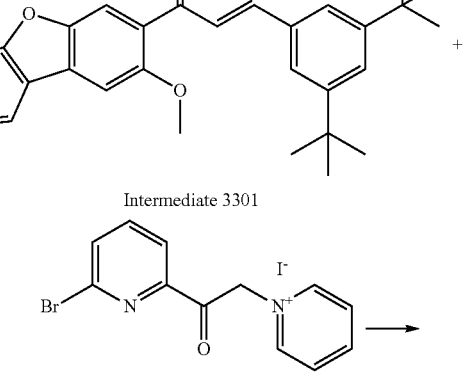

Intermediate 3301

Intermediate 3108

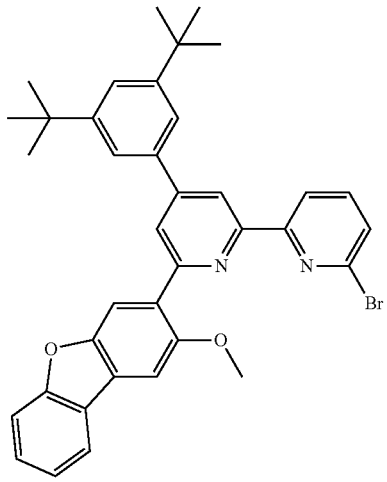

Intermediate 3208

The Intermediate 3301 (0.1 mol), the Intermediate 3108 (0.11 mol), ammonium acetate (1 mmol) and acetic acid (300 ml) are put into a round-bottom flask, and heated to reflux, react for 10 hours under a nitrogen atmosphere. After finished reaction, cooling naturally, part of the acetic acid is removed under reduced pressure, and a yellow solid is separated out. The solid is filtered out by suction, washed by

Example 13—Synthetizing Intermediate 3308

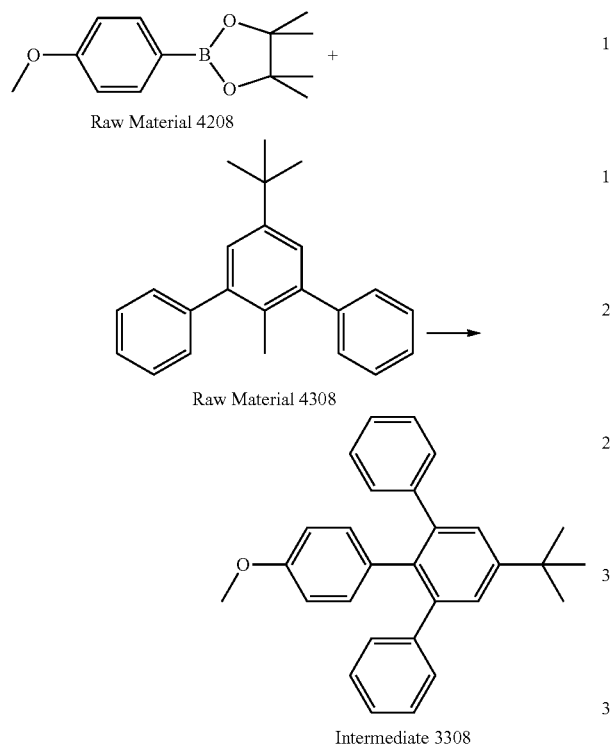

The Raw Material 4208 (50 mmol), the Raw Material 4308 (50 mmol), Pd(dppf)Cl$_2$ (2.5 mmol), cesium carbonate (0.1 mol), dioxane (120 ml) and water (20 ml) are put into a flask, heated to reflux under a nitrogen atmosphere, react for 8 hours. After finished reaction, the dioxane is spun off, then the reaction liquid is extracted by dichloromethane, and organic phase solution is collected. After evaporating out a solvent, a crude product is separated by silica gel column chromatography to obtain a transparent oily product with yield of 82%.

Example 14—Synthetizing Intermediate 3408

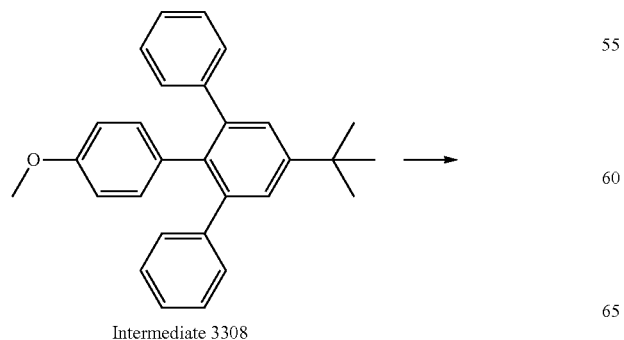

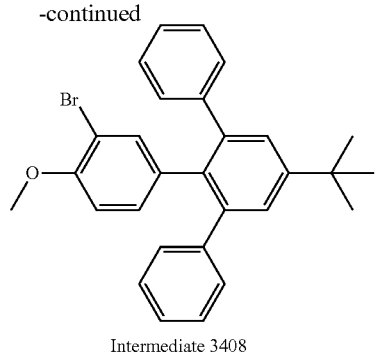

The Intermediate 3308 (40 mmol) is added to a flask where dichloromethane (100 ml) is subsequently added, then stirred to be dissolved, and then dichloromethane solution of bromine (42 mmol) is slowly added dropwise through a dropping funnel, then the mixture reacts at room temperature for 6 hours. After finished reaction, sodium bisulfite solution (5%) is added and stirred to quench the reaction, after separating out and collecting an organic phase, the aqueous phase is extracted by dichloromethane, and the organic phase is collected. After evaporating out a solvent, a crude product is separated by silica gel column chromatography to obtain a transparent white solid with yield of 85%.

Example 15—Synthetizing Intermediate 3508

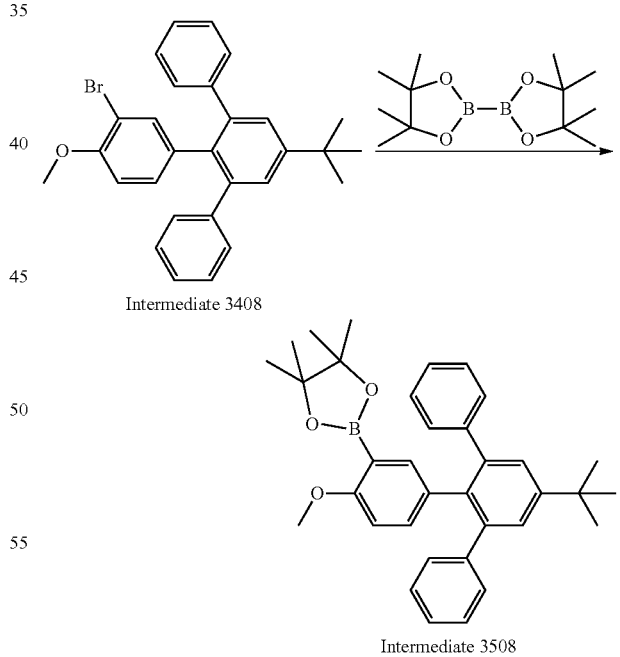

The Raw material 3408 (30 mmol), pinacol diborate (33 mmol), Pd(dppf)Cl$_2$ (1.5 mmol), potassium acetate (60 mol) and dioxane (100 ml) are put into a round-bottom flask, and heated to reflux for 10 hours under a nitrogen atmosphere. After that, the dioxane is spun off, then water is added. The reaction liquid is extracted by ethyl acetate, after collecting an organic phase, a resolvent is spun off. An oily product with yield of 70% is obtained after being purified by silica gel column chromatography.

Example 16—Synthetizing Intermediate 3608

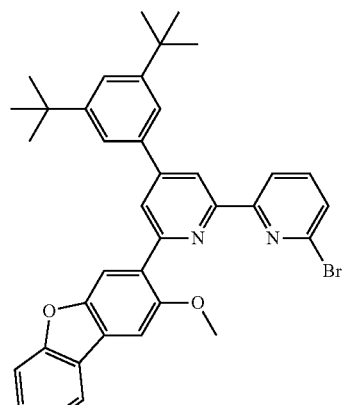

Intermediate 3208

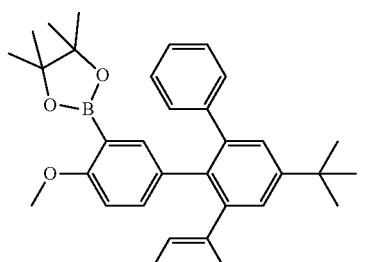

Intermediate 3508

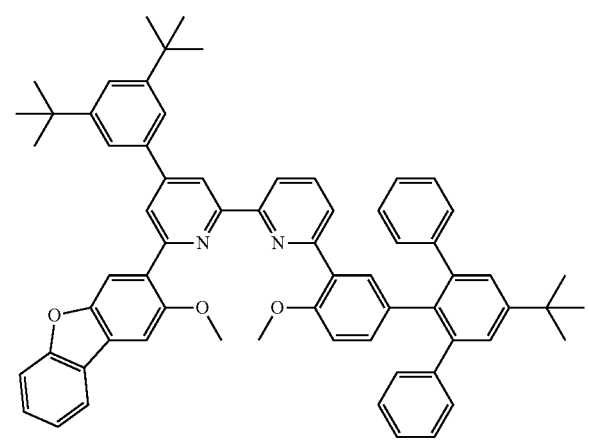

Intermediate 3608

The Intermediate 3208(18 mmol), the Intermediate 3508 (20 mmol), Pd(dppf)Cl2 (1 mmol), potassium carbonate (40 mmol), dioxane (80 ml) ad water (20 ml) are put into a round-bottom flask, heated to reflux under a nitrogen atmosphere, react for 10 hours. After finished reaction, the dioxane is spun off, then the reaction liquid is extracted by dichloromethane, and organic phase solution is collected. A crude product is separated by silica gel column chromatography to obtain a foamy yellow solid with yield of 72%.

Example 17—Synthetizing Ligand 2008

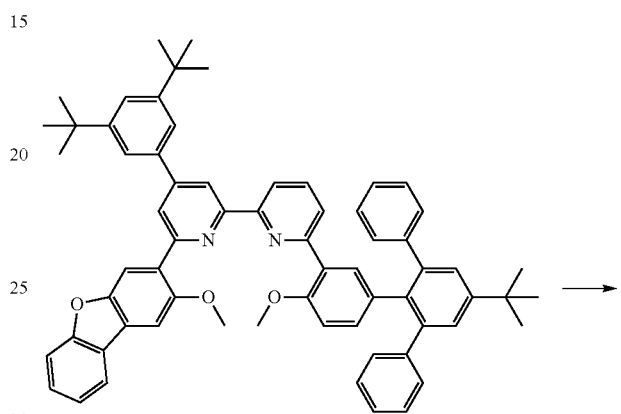

Intermediate 3608

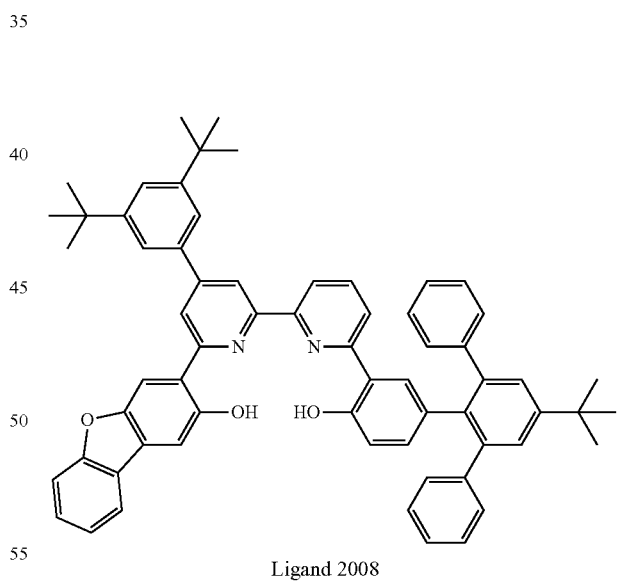

Ligand 2008

The Intermediate 3608(15 mmol) and pyridine hydrochloride (40 g) are put into a round-bottom flask, heated to 200° C. under a nitrogen atmosphere until melt-out and stirred for 6 hours, after finished reaction and cooling, a large amount of water is added, thus the pyridine hydrochloride dissolves and a product is separated out, then the product is filtered out by suction and washed by water and methanol. Finally, an orange-yellow solid with yield of 80% is obtained by silica gel column chromatography.

Example 18—Synthetizing Complex 1008

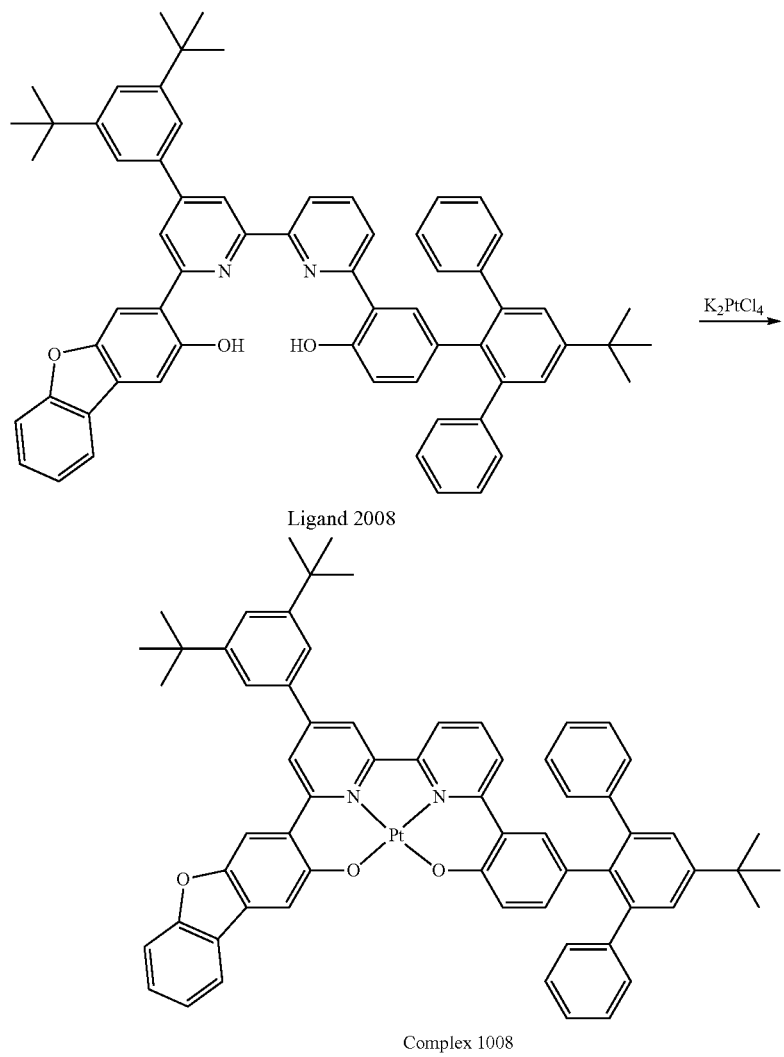

Ligand 2008

Complex 1008

The Ligand 2008 (10 mmol) is dissolved in dry DMSO where sodium tert-butoxide (22 mmol) and $K_2PtCl_4$ (22 mmol) are added, then the mixture is heated to 130° C. under a nitrogen atmosphere, and reacts for 12 hours. After finished reaction, it is cooled to room temperature naturally, and then an appropriate amount of water is added. A red solid is separated out. The solid is filtered out by suction and washed by water and methanol. The product is separated by silica gel column chromatography to obtain a red solid with yield of 76%.

Example 19—Synthetizing Intermediate 3120

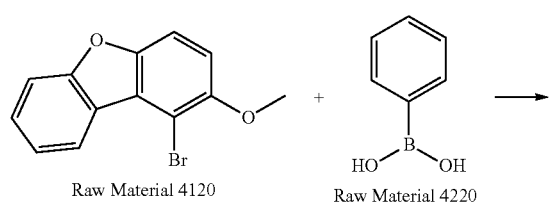

Raw Material 4120     Raw Material 4220

-continued

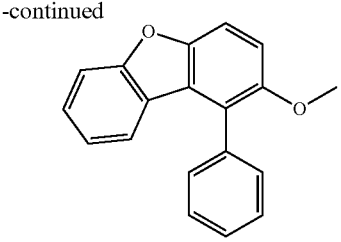

Intermediate 3120

A round-bottom flask is filled with the Raw Material 4120 (50 mmol), phenylboronic acid (4220)(6 mmol), Pd(dppf)Cl$_2$ (2.5 mmol), cesium carbonate (100 mmol), dioxane (100 ml) and water (20 ml), then the mixture is refluxed for 16 hours under a nitrogen atmosphere. After finished reaction, the dioxane is removed under reduced pressure, then pure water is added. The reaction solution is extracted by dichloromethane, after collecting an organic phase, a crude product is separated out by silica gel column chromatography to obtain an intermediate with yield of 51%.

Example 20—Synthetizing Intermediate 3220

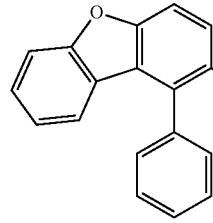

Intermediate 3120

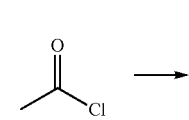

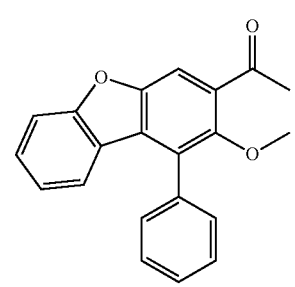

Intermediate 3220

The Intermediate 3120 (25 mmol) is added in a round-bottom flask, and dissolved by adding chloroform (100 ml) with stirring evenly, then aluminum trichloride powder (30 mmol) is added at room temperature, after that acetyl chloride (30 mmol) is added. When rising to 60° C. and being stirred for 6 hours, the raw material is used up. The reaction liquid is stirred and washed by adding 1M hydrochloric acid solution(50 ml), then separated into layers to obtain an organic phase, and an inorganic phase is extracted by dichloromethane (30 80 ml), after that the organic solution amalgamated is washed by water to neutralization. The organic solution is dewatered by anhydrous MgSO$_4$, and the solvent is removed under reduced pressure to obtain a crude product. The crude product is recrystallized with n-hexane to obtain a white solid with yield of 60%.

Example 21—Synthetizing Intermediate 3320

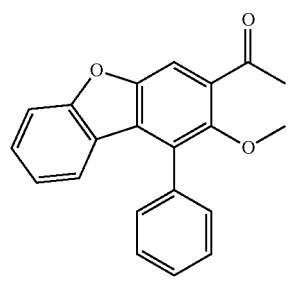

Intermediate 3220

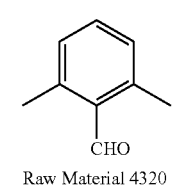

Raw Material 4320

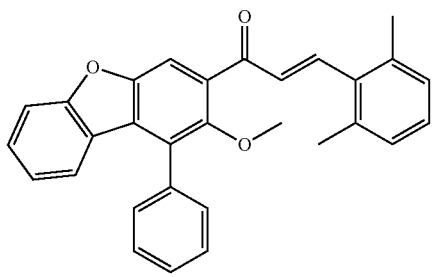

Intermediate 3320

A round-bottom flask is filled with the Intermediate 3220(14 mmol), the Raw Material 4320(16 mmol), which are stirred to dissolve by adding 80 mL of methanol, then potassium hydroxide aqueous solution (5 mL, 20 mmol) is slowly dropwise added into the mixture. After finished adding, the reaction mixture is heated to 50° C. under a nitrogen atmosphere and stirred for 10 hours. After the reaction mixture is cooled to room temperature, 4 M HCl solution is added to adjust the pH of the mixture to neutralization. a solid filtered out by suction are dissolved in an organic solvent, after filtering out an insoluble substance, and removing a solvent, a product is separated by silica gel column chromatography to obtain an intermediate with yield of 77%.

Example 22—Synthetizing Intermediate 3420

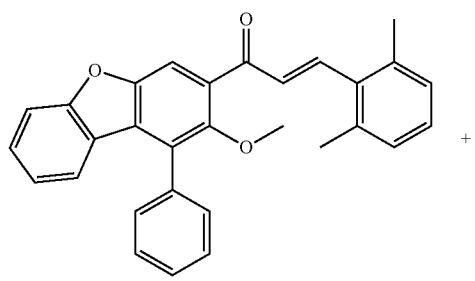

Intermediate 3320

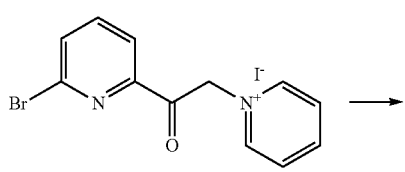

Intermediate 3108

-continued

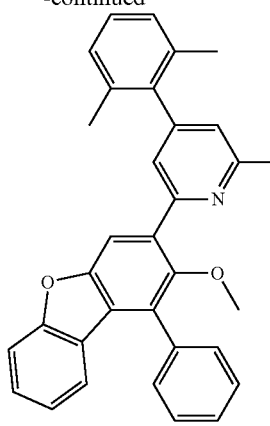

Intermediate 3420

The Intermediate 3320(9 mmol), the Intermediate 3108 (10 mmol), ammonium acetate (90 mmol) and acetic acid (90 ml) are put into a round-bottom flask, and heated to reflux, react for 10 hours under a nitrogen atmosphere. After finished reaction, cooling naturally, part of the acetic acid is removed under reduced pressure, and a yellow solid is separated out. The solid is filtered out by suction, washed by water and methanol, then heatedly beaten with methanol to obtain a yellow solid with yield of 78% by suction filtration and desiccation.

Example 23—Synthetizing Intermediate 3520

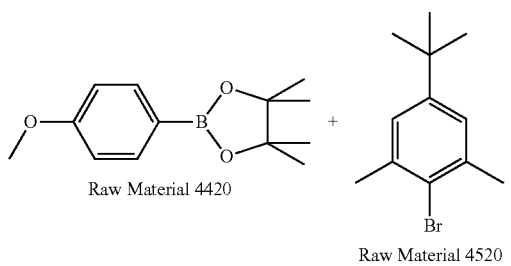

Intermediate 3520

The Raw Material 4420(50 mmol), the Raw Material 4520(50 mmol), Pd(dppf)Cl$_2$ (2.5 mmol), cesium carbonate (0.1 mol), dioxane (120 ml) and water (20 ml) are put into a flask, heated to reflux under a nitrogen atmosphere, react for 8 hours. After finished reaction, the dioxane is spun off, then the reaction liquid is extracted by dichloromethane, and organic phase solution is collected. After evaporating out a solvent, a crude product is separated by silica gel column chromatography to obtain a transparent oily product with yield of 81%.

Example 24—Synthetizing Intermediate 3620

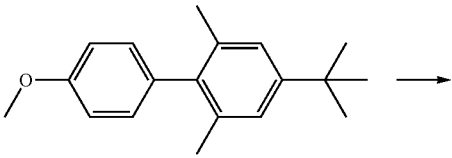

Intermediate 3520

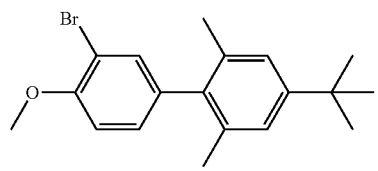

Intermediate 3620

The Intermediate 3520(40 mmol) is added to a flask where dichloromethane (100 ml) is subsequently added, then stirred to be dissolved, and then dichloromethane solution of bromine (42 mmol) is slowly added dropwise through a dropping funnel, then the mixture reacts at room temperature for 5 hours. After finished reaction, sodium bisulfite solution (5%) is added and stirred to quench the reaction, after separating out and collecting an organic phase, the aqueous phase is extracted by dichloromethane, and the organic phase is collected. After evaporating out a solvent, a crude product is separated by silica gel column chromatography to obtain a transparent white solid with yield of 76%.

Example 25—Synthetizing Intermediate 3720

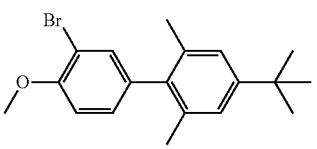 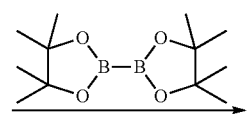

Intermediate 3620

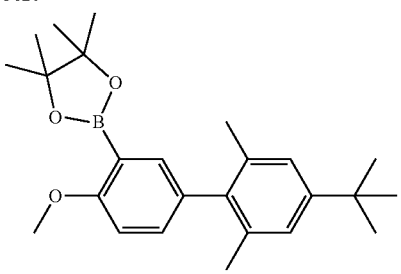

Intermediate 3720

The Raw material 3620(25 mmol), pinacol diborate (30 mmol), Pd(dppf)Cl2 (1 mmol), potassium acetate (50 mol) and dioxane (100 ml) are put into a round-bottom flask, and heated to reflux for 10 hours under a nitrogen atmosphere. After that, the dioxane is spun off, then water is added. The reaction liquid is extracted by ethyl acetate, after collecting an organic phase, a resolvent is spun off. An oily product with yield of 64% is obtained after being purified by silica gel column chromatography.

Example 26—Synthetizing Intermediate 3820

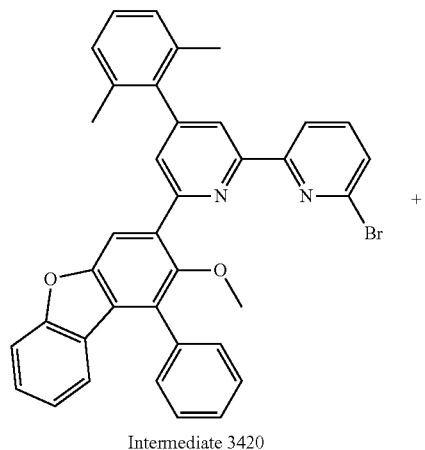

Intermediate 3420

Intermediate 3720

Intermediate 3820

The Intermediate 3420(15 mmol), the Intermediate 3720 (16 mmol), Pd(dppf)Cl$_2$(0.8 mmol), potassium carbonate (30 mmol), dioxane (80 ml) ad water (20 ml) are put into a round-bottom flask, heated to reflux under a nitrogen atmosphere, react for 15 hours. After finished reaction, the dioxane is spun off, then the reaction liquid is extracted by dichloromethane, and organic phase solution is collected. A crude product is separated by silica gel column chromatography to obtain a foamy yellow solid with yield of 70%.

Example 27—Synthetizing Ligand 2020

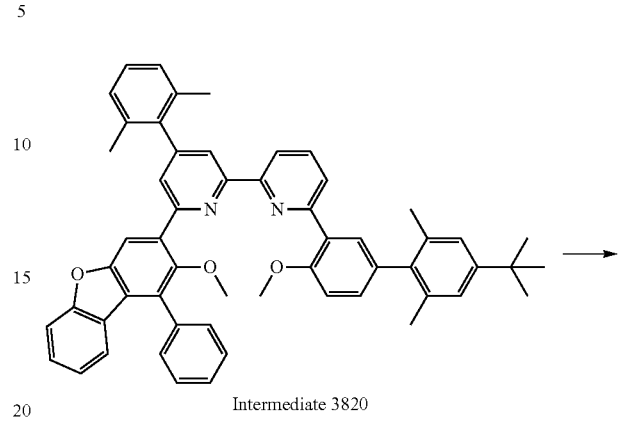

Intermediate 3820

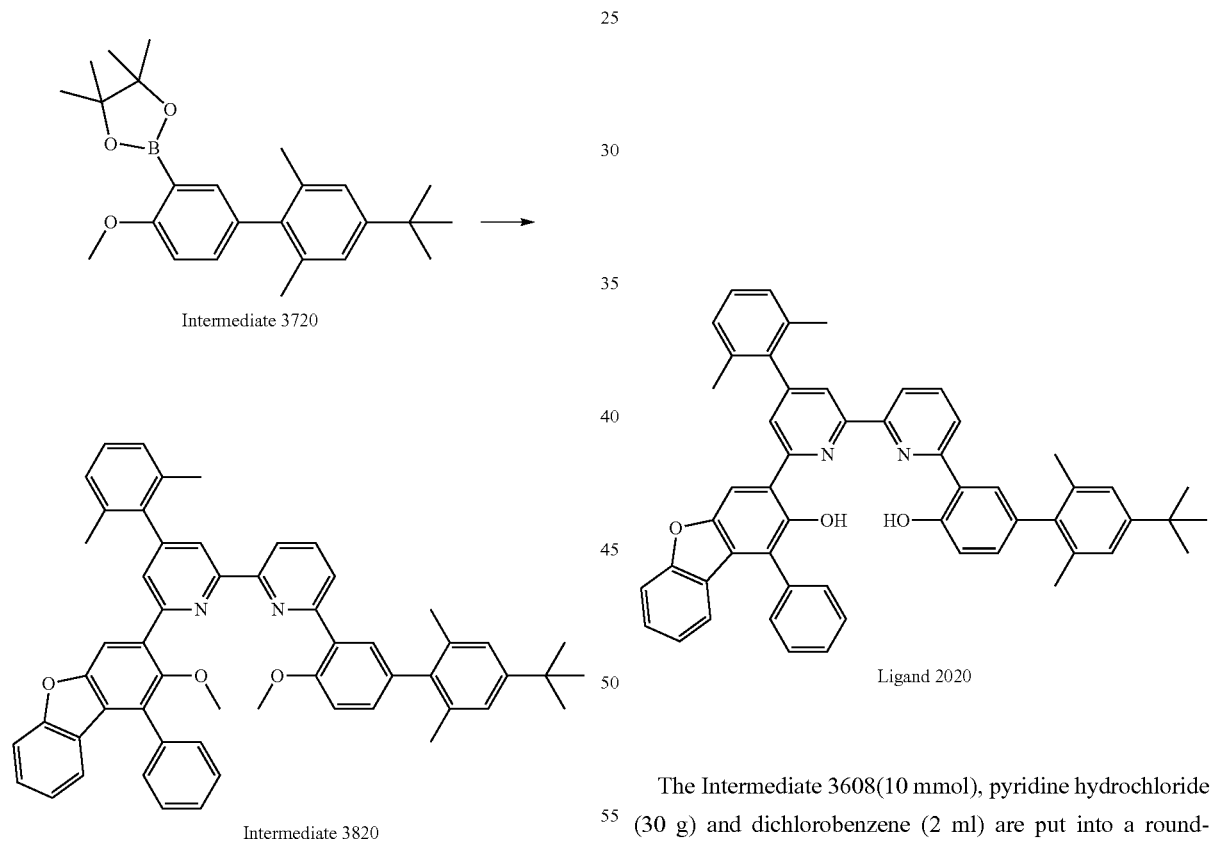

Ligand 2020

The Intermediate 3608(10 mmol), pyridine hydrochloride (30 g) and dichlorobenzene (2 ml) are put into a round-bottom flask, heated to 200° C. under a nitrogen atmosphere until melt-out and stirred for 6 hours, after finished reaction and cooling, a large amount of water is added, thus the pyridine hydrochloride dissolves and products are separated out. The products are extracted by dichloromethane and an organic phase is collected, then the products are washed by water. An orange-yellow solid with yield of 78% is obtained after separating by silica gel column chromatography.

Example 28—Synthetizing Complex 1020

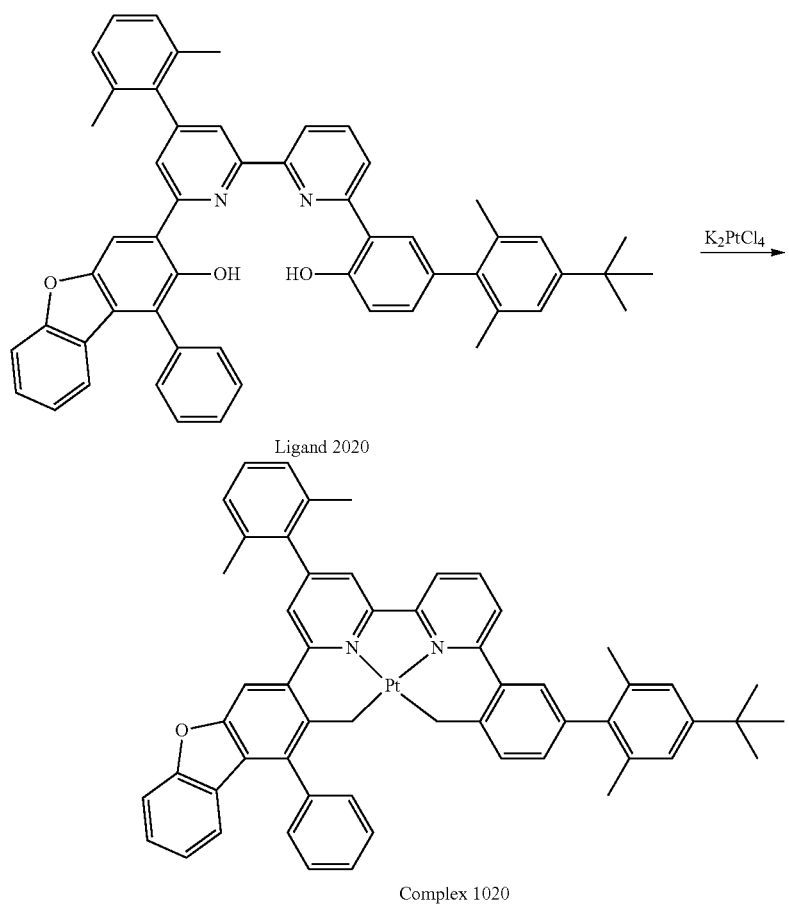

The Ligand 2010 (7 mmol) is dissolved in dry DMSO where sodium tert-butoxide (10 mmol) and K₂PtCl₄ (10 mmol) are added, then the mixture is heated to 130° C. under a nitrogen atmosphere, and reacts for 12 hours. After finished reaction, it is cooled to room temperature naturally, and then an appropriate amount of water is added. A red solid is separated out. The solid is filtered out by suction and washed by water and methanol. The product is separated by silica gel column chromatography to obtain a red solid with yield of 60%. Ms(ESI): 964.3 (M+H).

Example 29—Key Properties of the OLED Made of the Complex 1001

All OLEDs adopt the simple structure of ITO/HATCN (10 nm)/NPD (40 nm)/CBP: Complex 1001 (20 nm)/Balq (10 nm)/Alq$_3$ (40 nm)/LiF (1 nm)/Al (100 nm). This device displays red light. The table shows the device performance:

| doping concentration | EQE (%) |  |  | CIE (x, y) |
| --- | --- | --- | --- | --- |
|  | Max | 100 cd/m² | 1000 cd/m² |  |
| 5 wt % | 8.6 | 7.8 | 5.2 | (0.67, 0.29) |
| 10 wt % | 9.2 | 8.0 | 5.4 | (0.68, 0.29) |

Example 30—Key Properties of the OLED Made of the Complex 1008

All OLEDs adopt the simple structure of ITO/HATCN (10 nm)/NPD (40 nm)/CBP: Complex 1008 (20 nm)/Balq (10 nm)/Alq$_3$ (40 nm)/LiF (1 nm)/Al (100 nm). The table shows the device performance:

| doping concentration | EQE (%) |  |  | CIE (x, y) |
| --- | --- | --- | --- | --- |
|  | Max | 100 cd/m² | 1000 cd/m² |  |
| 5 wt % | 8.8 | 7.9 | 5.6 | (0.66, 0.30) |
| 10 wt % | 9.4 | 8.3 | 5.8 | (0.66, 0.29) |

Comparative Example 1—Key Properties of the OLED Made of the Complex 1025 in Reference Documents All OLEDs adopt the simple structure of ITO/HATCN (10 nm)/NPD (40 nm)/CBP: Complex 1025 (20 nm)/Balq (10 nm)/Alq$_3$ (40 nm)/LiF (1 nm)/Al (100 nm). At a doping concentration (5 wt %), due to strong intermolecular interaction and aggregated emission, the device has poor efficiency and emits a yellow light instead of a deep red light. The table shows the device performance:

| doping concentration | EQE (%) Max | 100 cd/m² | 1000 cd/m² | CIE (x, y) |
|---|---|---|---|---|
| 5 wt % | 3.2 | 2.5 | 1.8 | (0.43, 0.55) |

Comparative Example 2—Key Properties of the OLED Made of the Complex 1026 in Reference Documents All OLEDs adopt the simple structure of ITO/HATCN (10 nm)/NPD (40 nm)/CBP: Complex 1026 (20 nm)/Balq (10 nm)/Alq₃ (40 nm)/LiF (1 nm)/Al (100 nm). At a doping concentration (5 wt %), due to strong intermolecular interaction and aggregated emission, the device has poor efficiency and emits a yellow light instead of a deep red light. The table shows the device performance:

| doping concentration | EQE (%) Max | 100 cd/m² | 1000 cd/m² | CIE (x, y) |
|---|---|---|---|---|
| 5 wt % | 3.6 | 2.8 | 1.9 | (0.42, 0.56) |

The structures of the materials involved in each device are as follows:

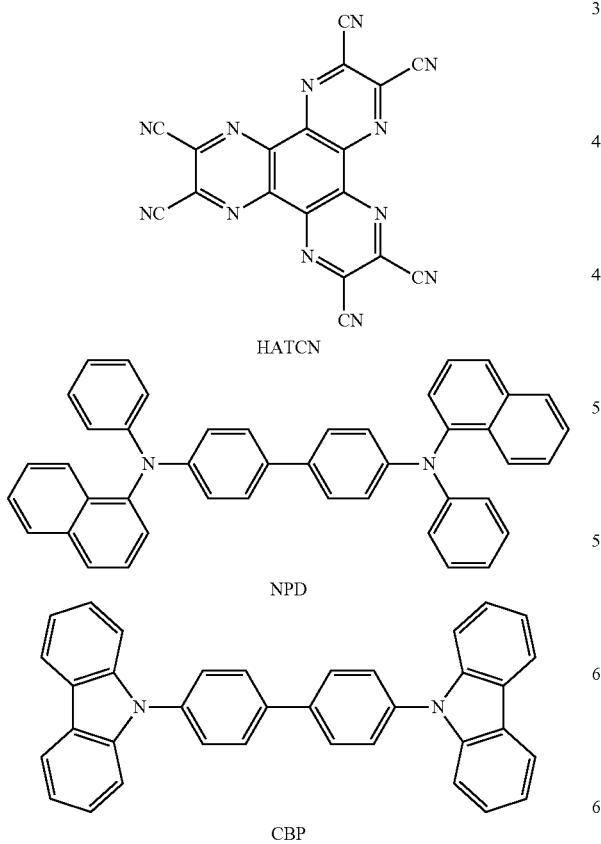

HATCN

NPD

CBP

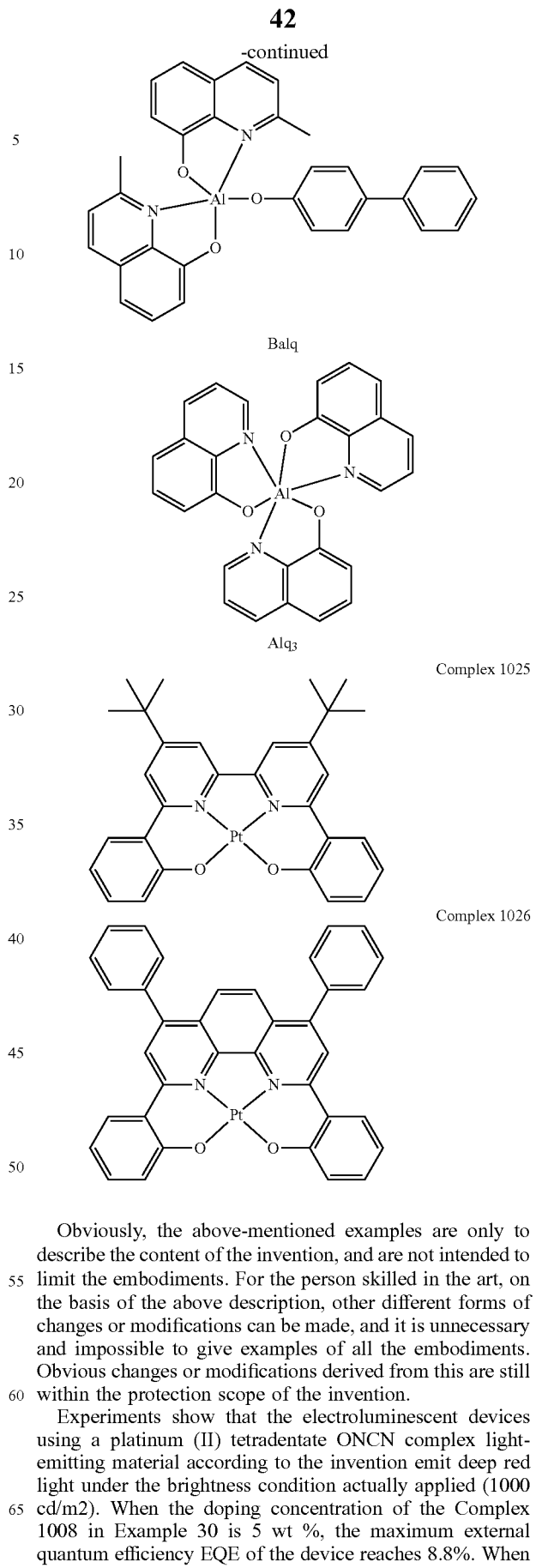

Balq

Alq₃

Complex 1025

Complex 1026

Obviously, the above-mentioned examples are only to describe the content of the invention, and are not intended to limit the embodiments. For the person skilled in the art, on the basis of the above description, other different forms of changes or modifications can be made, and it is unnecessary and impossible to give examples of all the embodiments. Obvious changes or modifications derived from this are still within the protection scope of the invention.

Experiments show that the electroluminescent devices using a platinum (II) tetradentate ONCN complex light-emitting material according to the invention emit deep red light under the brightness condition actually applied (1000 cd/m2). When the doping concentration of the Complex 1008 in Example 30 is 5 wt %, the maximum external quantum efficiency EQE of the device reaches 8.8%. When the doping concentration is increased to 10 wt %, the electroluminescence spectrum does not change much, and the doping concentration having an effect on the device efficiency is not obviously observed. The maximum external quantum efficiency EQE reaches 9.4%. In the Comparative Example 1, using the same device structure, when the doping concentration of the Complex 1025 is 5 wt %, it has been observed that an excimer at this concentration has an effect on the device performance, and its maximum external quantum efficiency is only 3.2%. A yellow light is emitted. when the doping concentration is 5 wt %, the maximum external quantum efficiency of the device manufactured by using the Complex 1026 in the Comparative Example 2 is only 3.6%. A yellow light is emitted. In contrast, at a moderate doping concentration, the platinum (II) tetradentate ONNO complex light-emitting material according to the invention has the device efficiency which is significantly improved, and emits a deep red light. At the doping concentration (10 wt %), the platinum (II) complex light-emitting material in the light-emitting layer of electroluminescent device can maintain red light emission, which is more suitable for industrial manufacturing systems and commercial applications.

What is claimed is:

1. A platinum (II) tetradentate ONCN complex light-emitting material having a chemical structure of Formula (I),

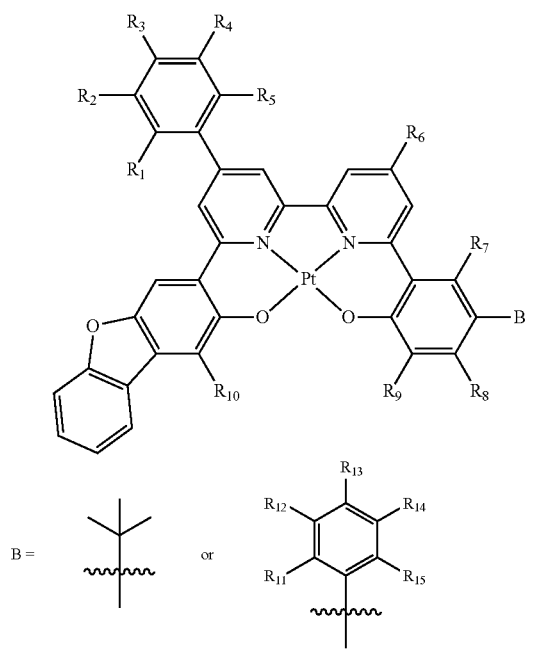

wherein:

$R_1$-$R_{10}$ are independently a hydrogen atom, a deuterium atom, a halogen, a hydroxyl group, an unsubstituted alkyl group, a halogenated alkyl group, a deuterated alkyl group, a cycloalkyl group, an unsubstituted aryl group, a halogenated aryl group, an acyl group, an alkoxyl group, an acyloxyl group, an amino group, a nitro group, an acylamino group, an aralkyl group, a cyano group, a carboxyl group, a sulfonyl group, a styryl group, an amino carboxyl group, a carbamoyl group, an aryloxy carboxyl group, a phenoxy carboxyl or epoxy carboxyl group, a carbazole group or a diphenylamine group, or $R_1$-$R_{10}$ independently form a 5-8 membered ring with adjacent groups, and $R_1$-$R_{10}$ are not hydrogen at the same time;

B presents an anti-aggregation group, and wherein $R_{11}$-$R_{15}$ are independently a hydrogen atom, a deuterium atom, a halogen, an unsubstituted alkyl group, a halogenated alkyl group, a deuterated alkyl group, a cycloalkyl group, an unsubstituted aryl group, a halogenated aryl group, a C1-C10 alkyl substituted aryl group, a cyano group, a carbazolyl group, or a C1-C10 alkyl substituted carbazolyl group.

2. The light-emitting material according to claim 1, wherein:

$R_1$-$R_{10}$ are independently a hydrogen atom, a deuterium atom, a halogen, a hydroxyl group, an unsubstituted alkyl group having 1 to 6 carbon atoms, a halogenated alkyl group having 1 to 6 carbon atoms, a deuterated alkyl group having 1 to 2 carbon atoms, a five- or six-membered cycloalkyl group, an unsubstituted aryl group having 6 to 10 carbon atoms, a halogenated aryl group having 6 to 10 carbon atoms, an alkoxyl group having 1 to 6 carbon atoms, an amino group, a nitro group, a cyano group, a carbazolyl group, or a diphenylamine group, or $R_1$-$R_{10}$ independently form a 5-8 membered ring with adjacent groups, and $R_{11}$-$R_{15}$ are independently a hydrogen atom, a deuterium atom, a halogen, an unsubstituted alkyl group having 1 to 6 carbon atoms, a halogenated alkyl group having 1 to 6 carbon atoms, a five-or six-membered cycloalkyl group, an unsubstituted aryl group having 6 to 10 carbon atoms, a halogenated aryl group having 6 to 10 carbon atoms, a C1-C4 alkyl substituted aryl group having 6 to 10 carbon atoms, a cyano group, a carbazolyl group, or a C1-C4 alkyl substituted carbazolyl group.

3. The light-emitting material according to claim 2, wherein $R_7$, $R_8$ are independently a hydrogen atom.

4. The light-emitting material according to claim 3, wherein $R_6$, $R_9$ and $R_{10}$ are independently a hydrogen atom, a fluorine atom, an unsubstituted alkyl group having 1 to 4 carbon atoms, a trifluoromethyl group or a phenyl group.

5. The light-emitting material according to claim 4, wherein:

$R_1$-$R_5$ are independently a hydrogen atom, a deuterium atom, a fluorine atom, an unsubstituted alkyl group having 1 to 4 carbon atoms, a halogenated alkyl group having 1 to 4 carbon atoms, a five- or six-membered cycloalkyl group, an unsubstituted aryl group having 6 to 10 carbon atoms, a fluorinated aryl group having 6 to 10 carbon atoms, and $R_{11}$-$R_{15}$ are independently a hydrogen atom, a deuterium atom, a fluorine atom, an unsubstituted alkyl group having 1 to 4 carbon atoms, a fluorinated alkyl group having 1 to 4 carbon atoms, a five- or six-membered cycloalkyl group, an unsubstituted aryl group having 6 to 10 carbon atoms, a halogenated aryl group having 6 to 10 carbon atoms, a C1-C4 alkyl substituted aryl group having 6 to 10 carbon atoms, a carbazolyl group, or a C1-C4 alkyl substituted carbazolyl group.

6. The light-emitting material according to claim 5, wherein $R_1$-$R_5$ are independently a hydrogen atom, a fluorine atom, an unsubstituted alkyl group having 1 to 4 carbon atoms, a trifluoromethyl group or a phenyl group.

7. The light-emitting material according to claim 6, wherein:

$R_1$, $R_3$ and $R_5$ are independently a hydrogen atom, and $R_2$ and $R_4$ are independently a hydrogen atom, a fluorine atom, an unsubstituted alkyl group having 1 to 4 carbon atoms, a trifluoromethyl group or a phenyl group.

8. The light-emitting material according to claim 7, wherein $R_{11}$-$R_{15}$ are independently a hydrogen atom, an unsubstituted alkyl group having 1 to 4 carbon atoms, a trifluoromethyl group or a phenyl group.

9. The light-emitting material according to claim 5, wherein:

$R_{12}$ and $R_{14}$ are independently a hydrogen atom, and $R_{11}$, $R_{13}$ and $R_{15}$ are independently a hydrogen atom, a fluorine atom, an unsubstituted alkyl group having 1 to 4 carbon atoms, a trifluoromethyl group, a phenyl group, a 4-tert-butylphenyl group, a naphthyl group or a carbazolyl group.

10. A platinum (II) tetradentate ONCN complex light-emitting material having one of the following chemical structural formulas:

Complex 1001

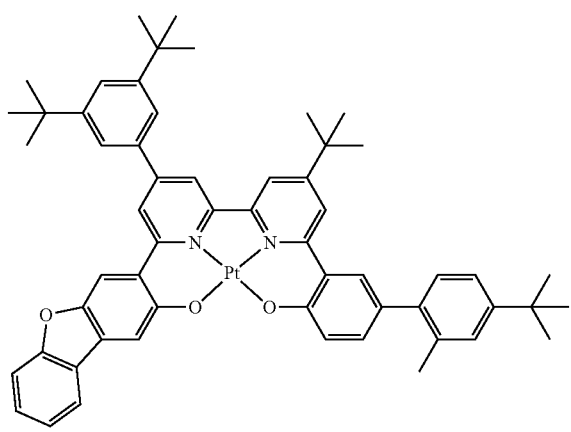

Complex 1002

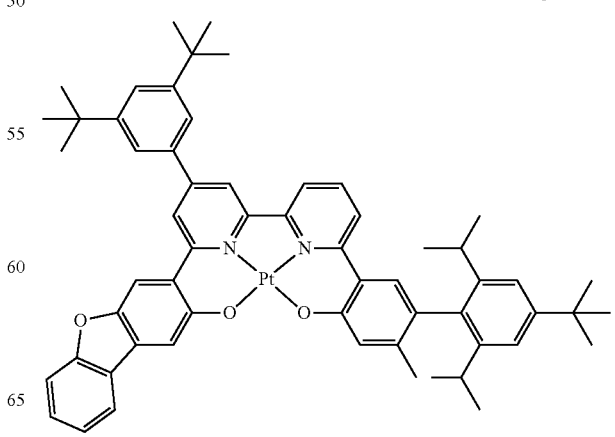

Complex 1003

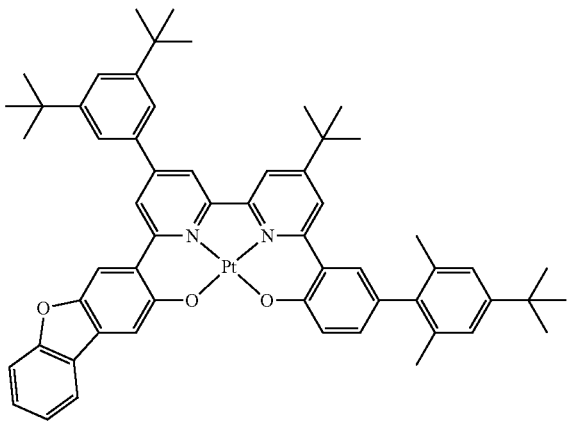

Complex 1004

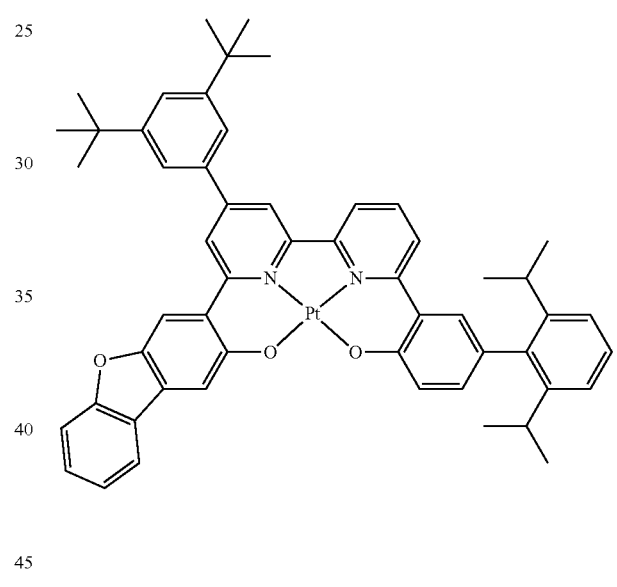

Complex 1005

Complex 1006
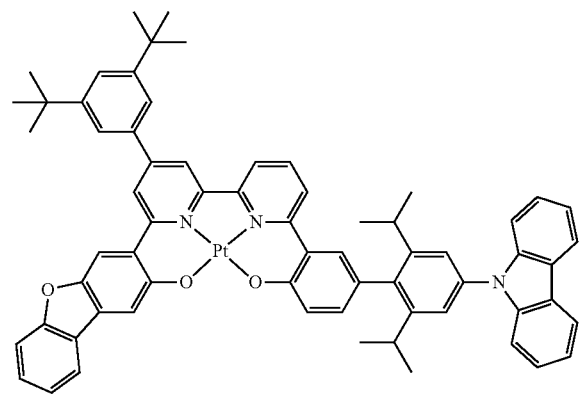
Complex 1007
Complex 1008
Complex 1009
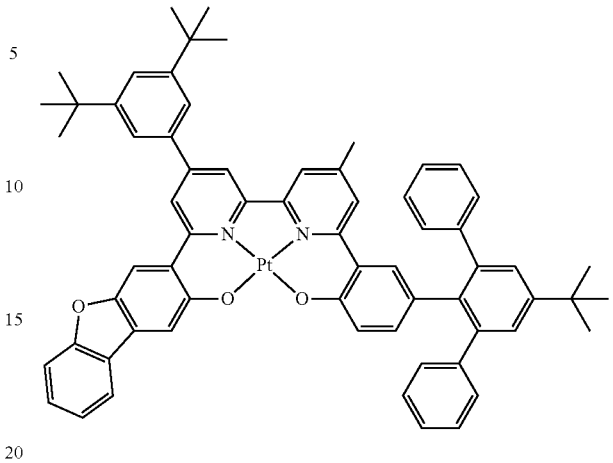
Complex 1010
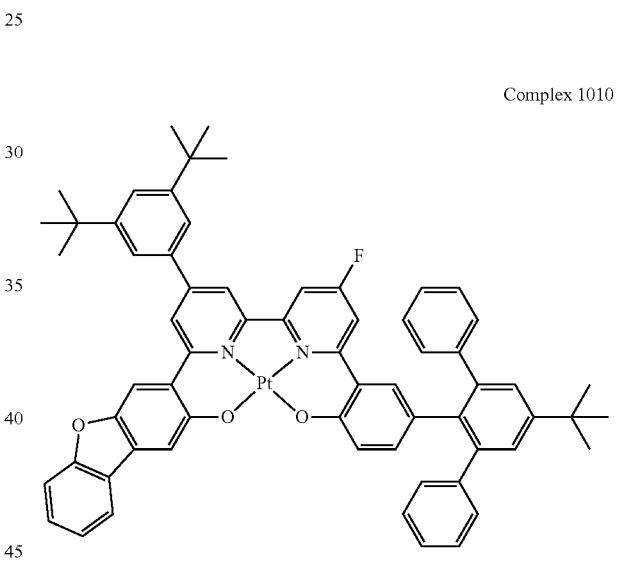
Complex 1011
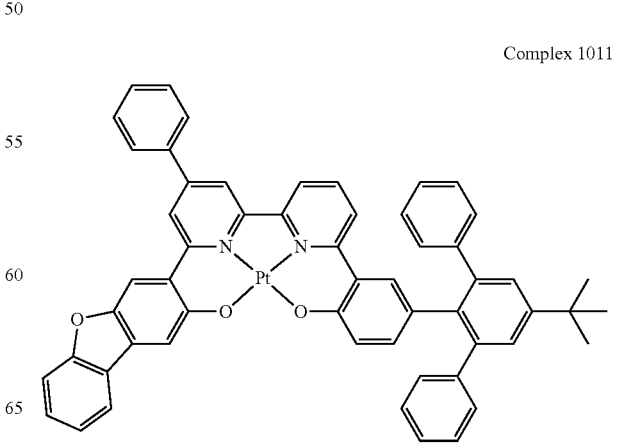

Complex 1012
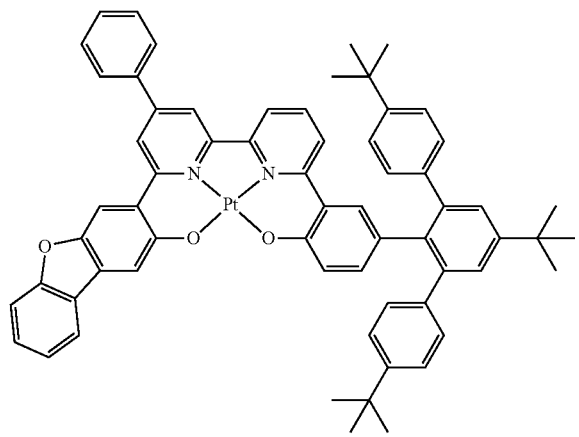
Complex 1015
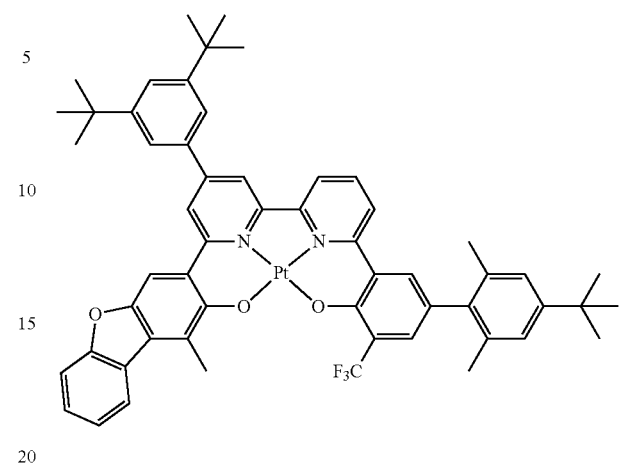
Complex 1013
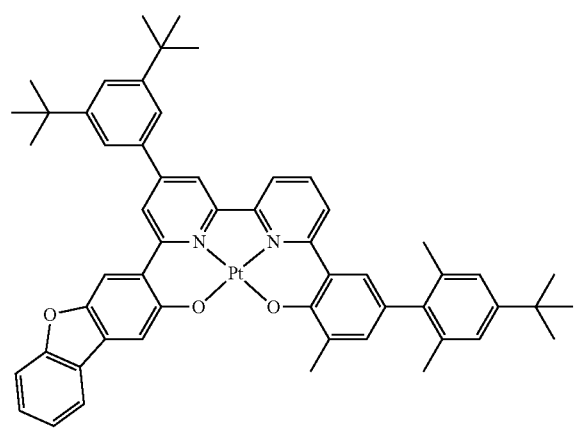
Complex 1016
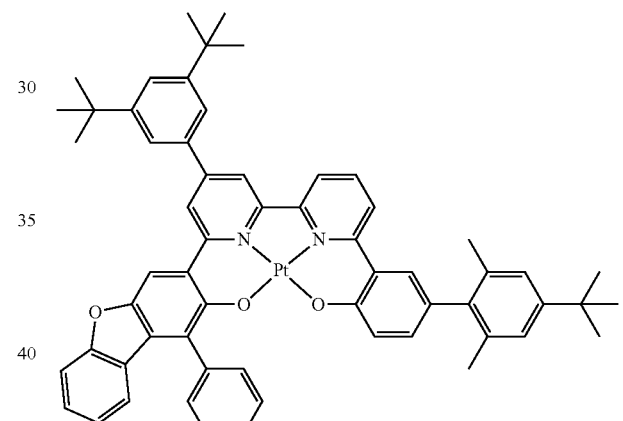
Complex 1014
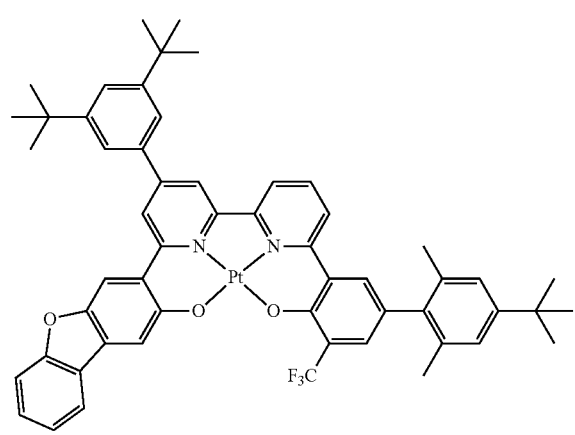
Complex 1017
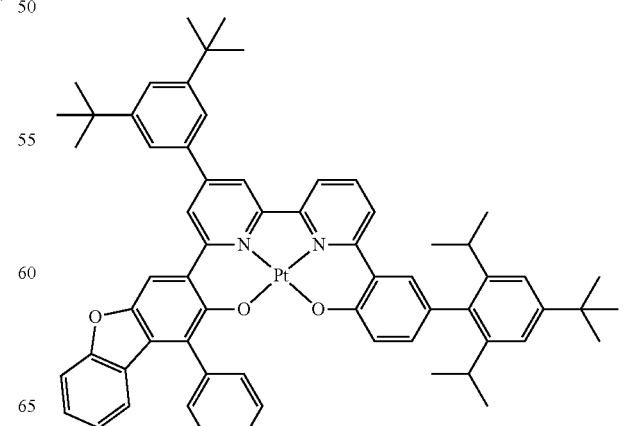

Complex 1018
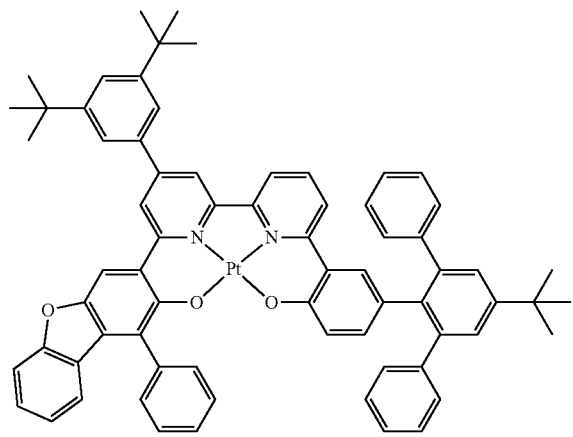
Complex 1019
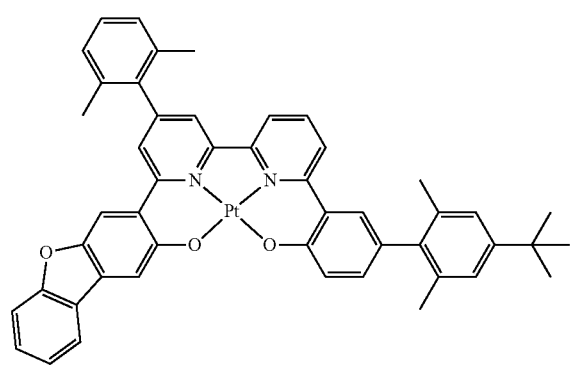
Complex 1020
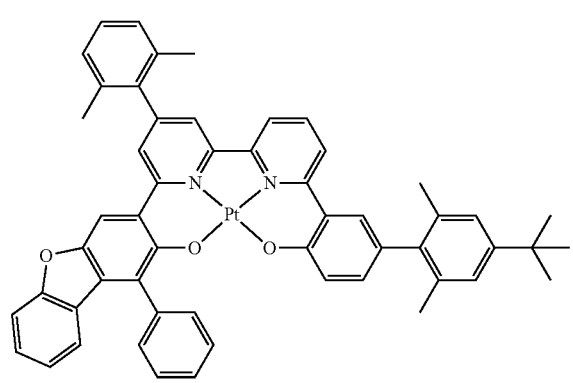
Complex 1021
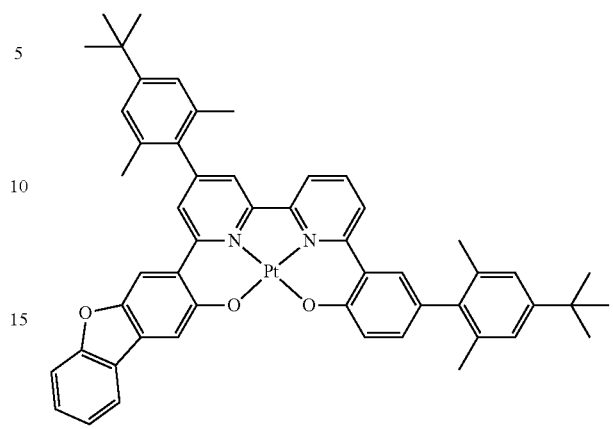
Complex 1022
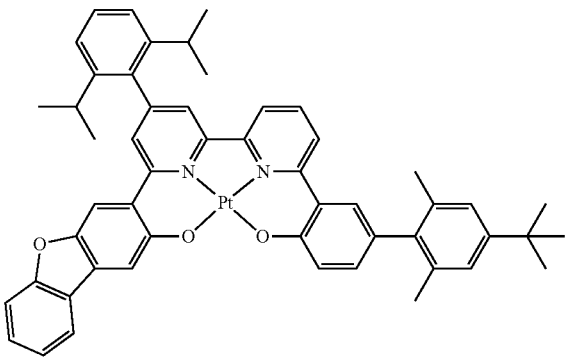
Complex 1023
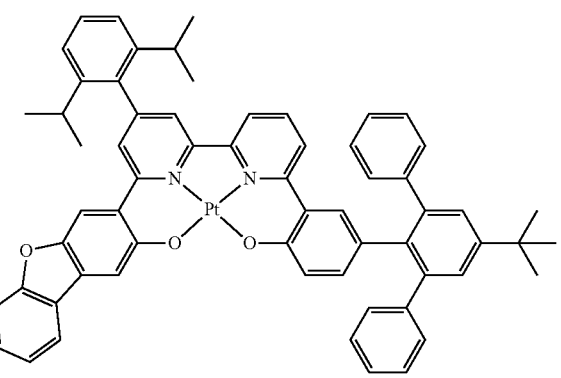

Complex 1024

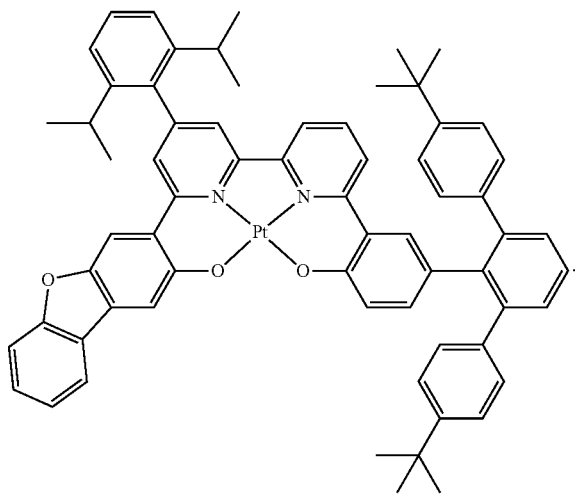

11. A ligand of said light-emitting material according to claim 1, having the following chemical structure:

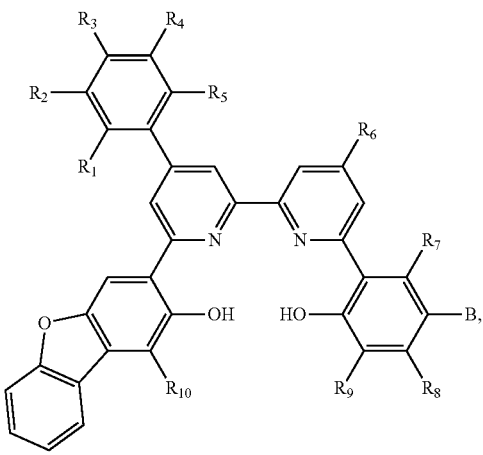

where

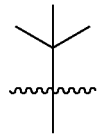
B =
or
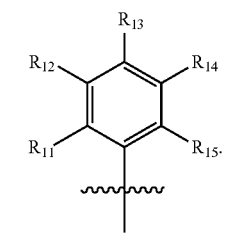

12. A preparation method of said light-emitting material according to claim 1, comprising:

using a substituted o-methoxydibenzo[b,d] furan ethyl ketone compound A and a substituted or unsubstituted benzaldehyde compound B as raw material to obtain a substituted or unsubstituted chalcone compound C under alkaline KOH conditions, mixing a substituted or unsubstituted 6-bromopyridyl ethyl ketone compound D with such pyridine as a solvent to obtain a pyridine salt intermediate E under iodine simple substance conditions, obtaining a pyridine ring intermediate F from the substituted or unsubstituted chalcone compound C and the pyridine salt intermediate E under ammonium acetate conditions, coupling the pyridine ring intermediate F with a o-methoxyphenyl boronic ester compound H by way of metal coupling to obtain an intermediate I, obtaining a ligand J from the intermediate I by way of demethylation reaction, and reacting the ligand J with a platinum compound under alkaline conditions to obtain a platinum (II) tetradentate ONCN complex light-emitting material after being purified, the chemical equations thereof being as follows:

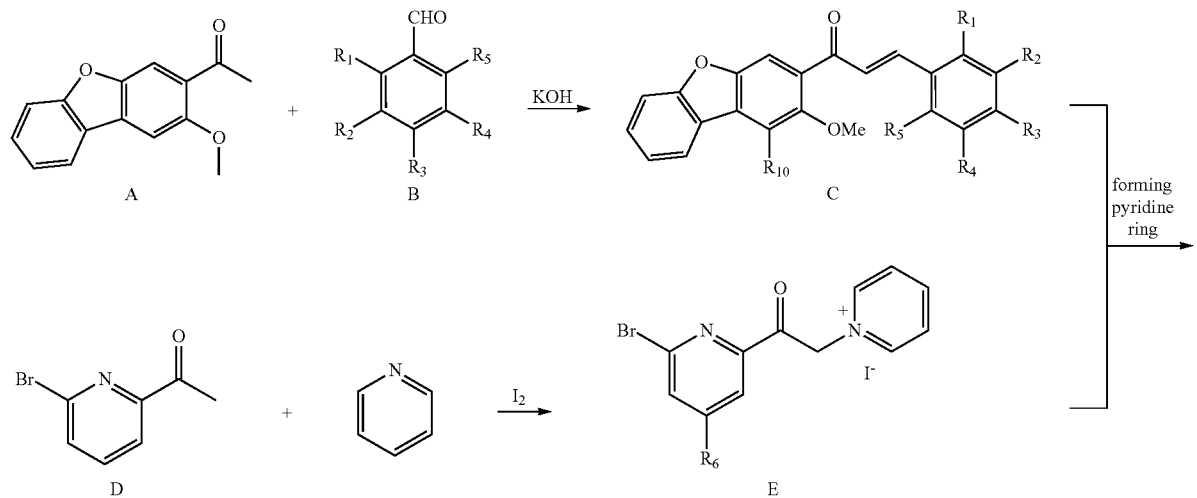

-continued
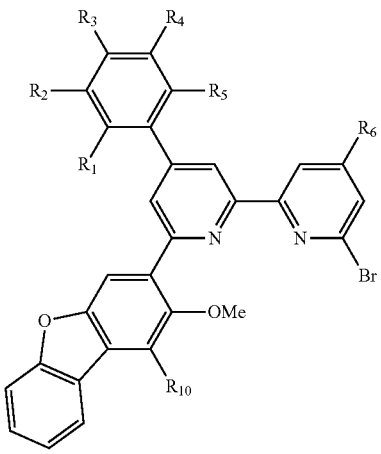
F
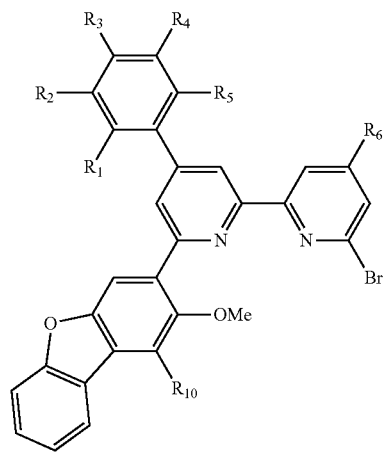 + 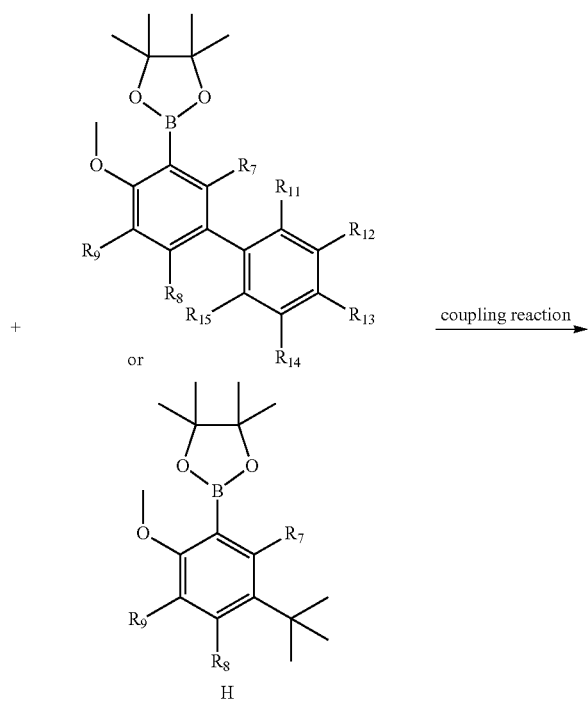 coupling reaction →
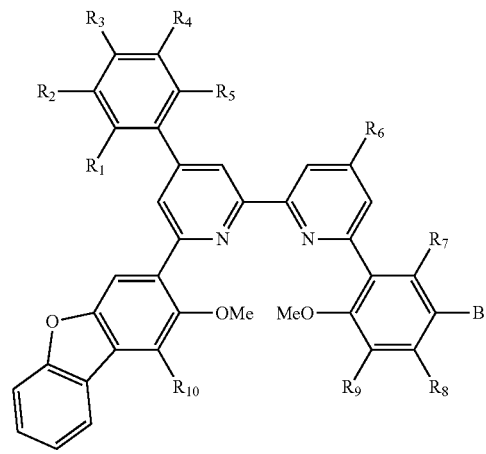
I -continued
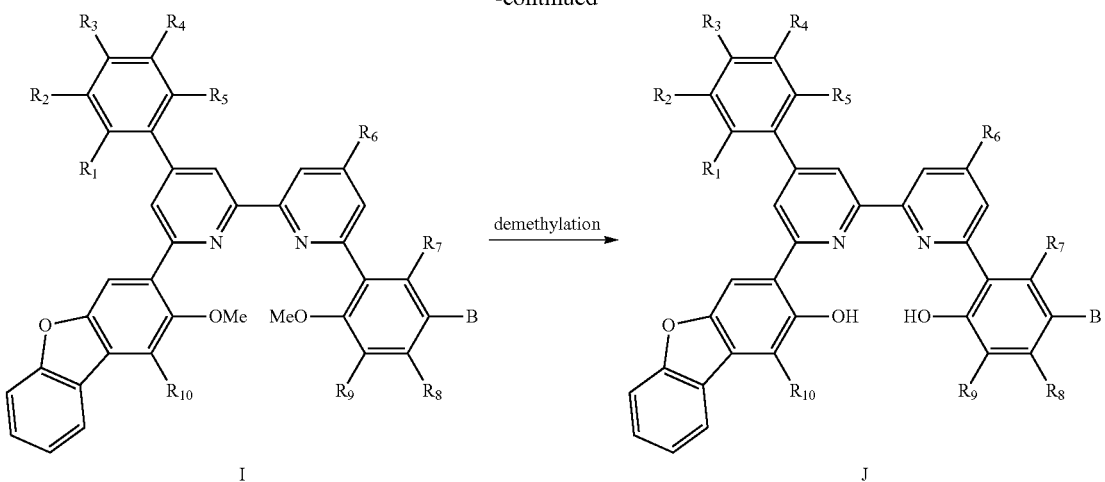
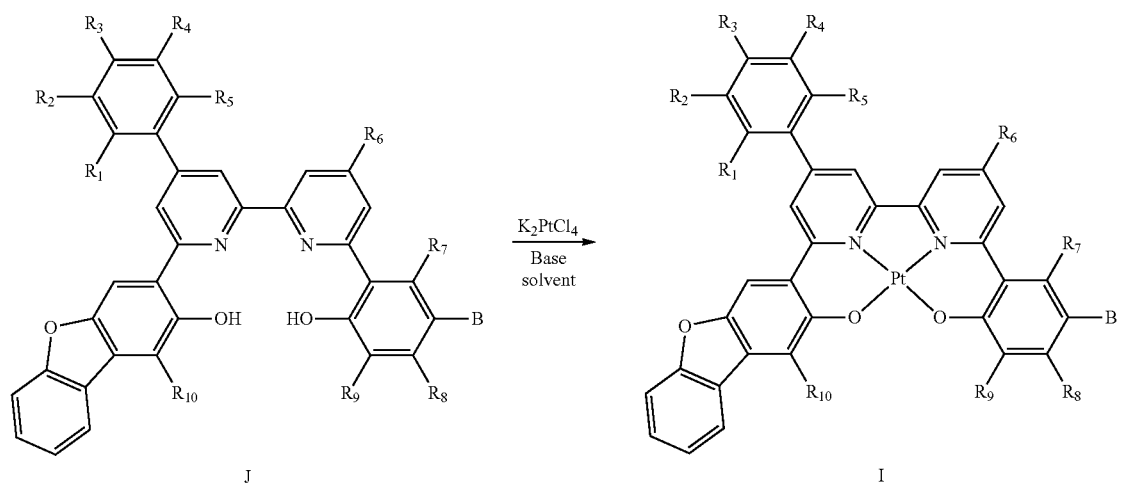
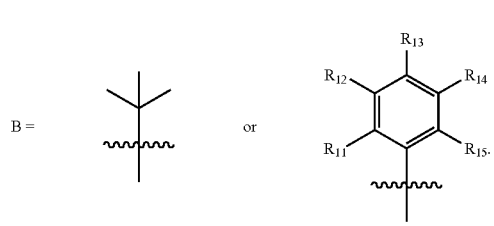

13. The preparation method according to claim 12, wherein said coupling reaction is carried out by using Pd(PPh$_3$)$_4$ as a catalyst under K$_2$CO$_3$ basic conditions.

14. The preparation method according to claim 12, wherein said ligand J reacts with platinum compound potassium tetrachloroplatinate in sodium tert-butoxide and solvent DMSO at 130° C.

15. An application of said light-emitting material according to claim 1 in organic electroluminescent devices.

16. A ligand of said light-emitting material according to claim 2, having the following chemical structure:

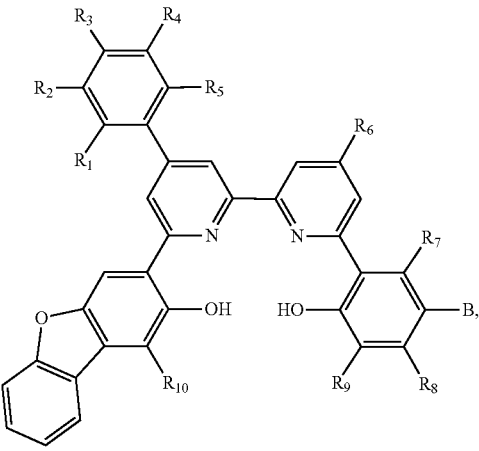

where

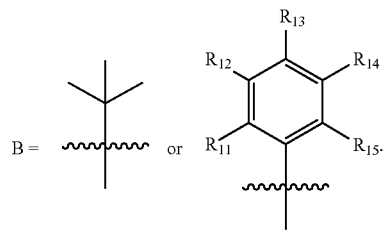

17. A preparation method of said light-emitting material according to claim 2, comprising:

using a substituted o-methoxydibenzo[b,d] furan ethyl ketone compound A and a substituted or unsubstituted benzaldehyde compound B as raw material to obtain a substituted or unsubstituted chalcone compound C under alkaline KOH conditions, mixing a substituted or unsubstituted 6-bromopyridyl ethyl ketone compound D with such pyridine as a solvent to obtain a pyridine salt intermediate E under iodine simple substance conditions, obtaining a pyridine ring intermediate F from the substituted or unsubstituted chalcone compound C and the pyridine salt intermediate E under ammonium acetate conditions, coupling the pyridine ring intermediate F with a o-methoxyphenyl boronic ester compound H by way of metal coupling to obtain an intermediate I, obtaining a ligand J from the intermediate I by way of demethylation reaction, and reacting the ligand J with a platinum compound under alkaline conditions to obtain a platinum (II) tetradentate ONCN complex light-emitting material after being purified, the chemical equations thereof being as follows:

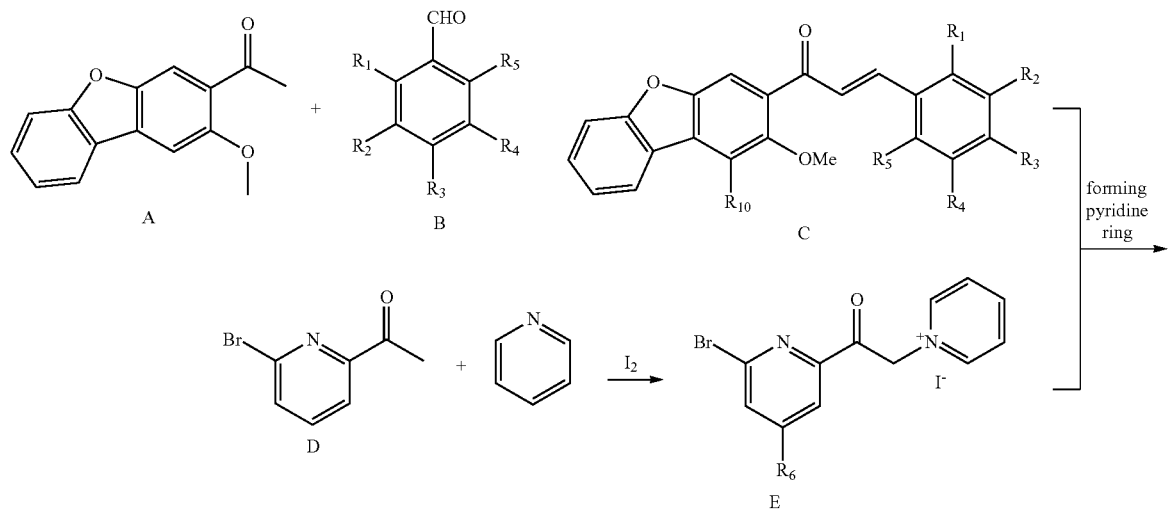

-continued
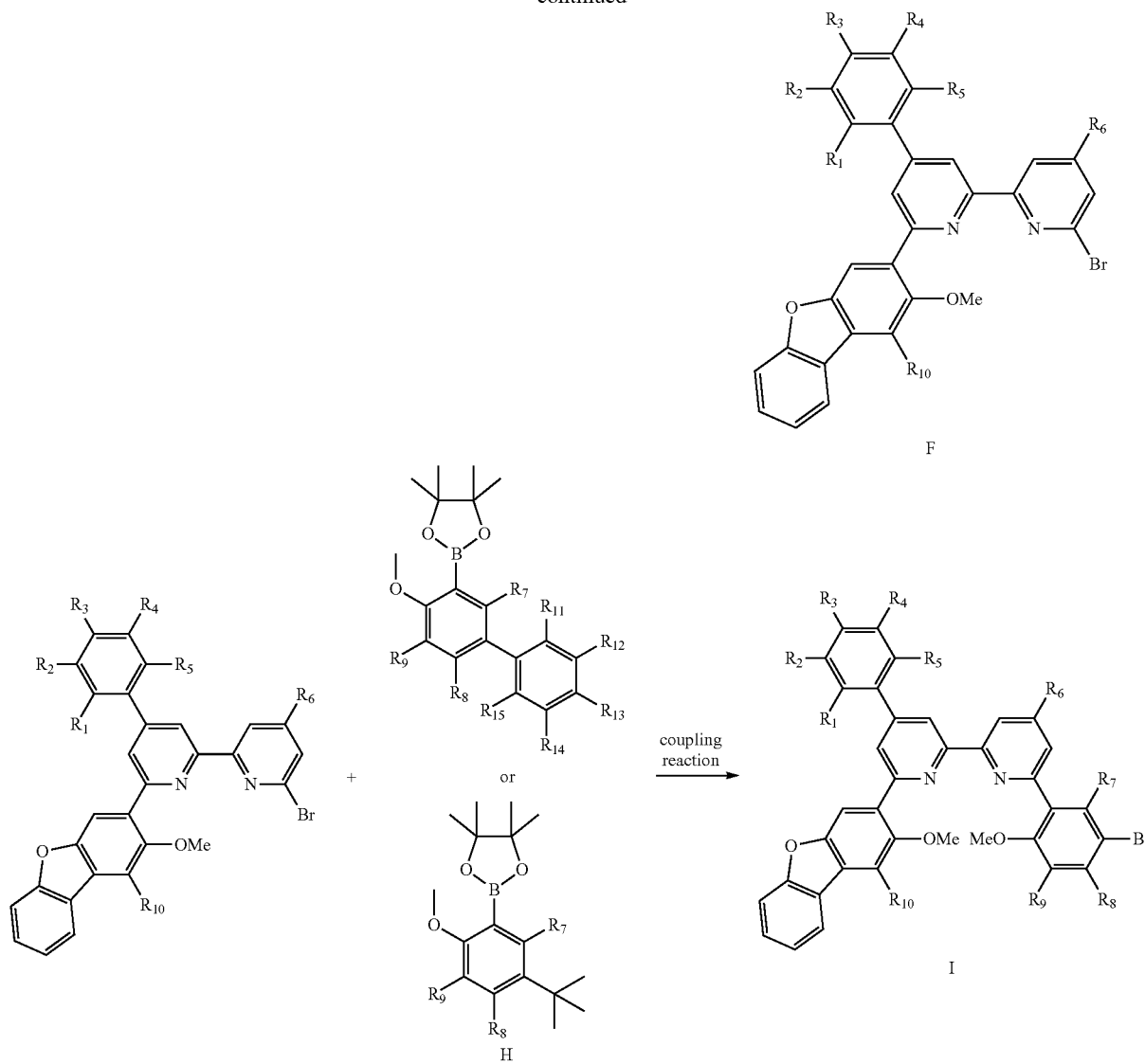
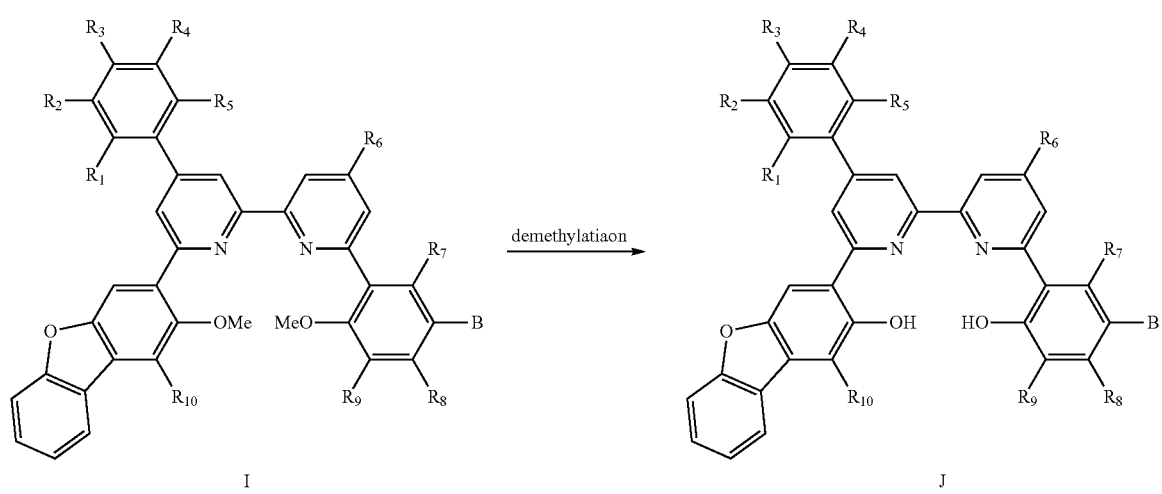

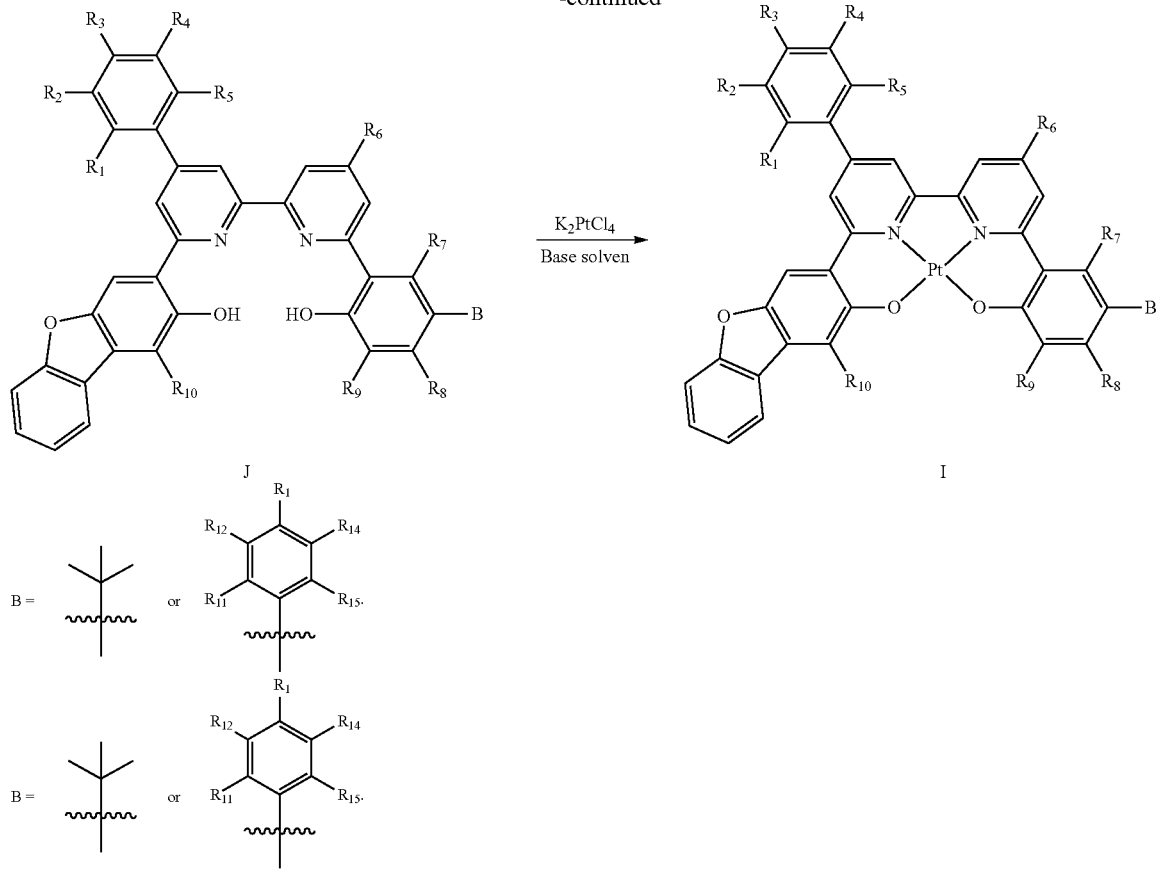

18. The preparation method according to claim 17, wherein said coupling reaction is carried out by using Pd(PPh$_3$)$_4$ as a catalyst under K$_2$CO$_3$ basic conditions.

19. The preparation method according to claim 17, wherein said ligand J reacts with platinum compound potassium tetrachloroplatinate in sodium tert-butoxide and solvent DMSO at 130° C.

20. An application of said light-emitting material according to claim 10 in organic electroluminescent devices.

* * * * *